(12) United States Patent
Martini et al.

(10) Patent No.: US 11,059,906 B2
(45) Date of Patent: Jul. 13, 2021

(54) ANTI-CCL2 AND ANTI-LOXL2 COMBINATION THERAPY FOR TREATMENT OF SCLERODERMA

(71) Applicant: SHIRE HUMAN GENETIC THERAPIES, INC., Lexington, MA (US)

(72) Inventors: Paolo G. V. Martini, Boston, MA (US); Madhusudan Natarajan, Waban, MA (US); Patrick Anthony John Haslett, Somerville, MA (US); Albert Barnes Seymour, Westborough, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/893,486

(22) PCT Filed: May 23, 2014

(86) PCT No.: PCT/US2014/039437
§ 371 (c)(1),
(2) Date: Nov. 23, 2015

(87) PCT Pub. No.: WO2014/190316
PCT Pub. Date: Nov. 27, 2014

(65) Prior Publication Data
US 2016/0083482 A1      Mar. 24, 2016

Related U.S. Application Data

(60) Provisional application No. 61/826,692, filed on May 23, 2013.

(51) Int. Cl.
| | | |
|---|---|---|
| C07K 16/40 | (2006.01) | |
| C07K 16/24 | (2006.01) | |
| A61K 39/00 | (2006.01) | |

(52) U.S. Cl.
CPC ............. *C07K 16/40* (2013.01); *C07K 16/24* (2013.01); *A61K 2039/505* (2013.01); *A61K 2039/507* (2013.01); *A61K 2039/54* (2013.01); *A61K 2039/545* (2013.01); *C07K 2317/24* (2013.01); *C07K 2317/31* (2013.01); *C07K 2317/54* (2013.01); *C07K 2317/55* (2013.01); *C07K 2317/622* (2013.01); *C07K 2317/626* (2013.01); *C07K 2317/92* (2013.01)

(58) Field of Classification Search
CPC ................................ C07K 16/40; C07K 16/24
See application file for complete search history.

(56) References Cited

U.S. PATENT DOCUMENTS

| | | |
|---|---|---|
| 4,166,452 A | 9/1979 | Generales, Jr. |
| 4,816,567 A | 3/1989 | Cabilly et al. |
| 4,956,778 A | 9/1990 | Naito |
| 5,091,513 A | 2/1992 | Huston et al. |
| 5,132,405 A | 7/1992 | Huston et al. |
| 5,601,819 A | 2/1997 | Wong et al. |
| 5,762,930 A | 6/1998 | Fanger et al. |
| 5,807,706 A | 9/1998 | Carter et al. |
| 5,959,083 A | 9/1999 | Bosslet et al. |
| 6,004,555 A | 12/1999 | Thorpe et al. |
| 6,010,902 A | 1/2000 | Ledbetter et al. |
| 6,060,285 A | 5/2000 | Lenz et al. |
| 9,176,139 B2 * | 11/2015 | Smith .................... C07K 16/40 |
| 2002/0025317 A1 | 2/2002 | Leung et al. |
| 2010/0166757 A1 * | 7/2010 | De Fougerolles ..... C07K 16/24 424/135.1 |
| 2011/0200606 A1 * | 8/2011 | McCauley ............. C07K 16/40 424/139.1 |

FOREIGN PATENT DOCUMENTS

| | | |
|---|---|---|
| WO | 9111465 A1 | 8/1991 |
| WO | 2009/017833 A2 | 2/2009 |
| WO | 2009035791 A1 | 3/2009 |
| WO | 2011/025962 A1 | 3/2011 |
| WO | 2013177264 A1 | 11/2013 |

OTHER PUBLICATIONS

Chanoki, et al. (Br. J. Dermatol. 1995;133(5):710-5).*
Manetti et al. (2010), Chapters, in D. Abraham et al. (eds.), Advances in Vascular Medicine, DOI 10.1007/978-1-84882-637-3_3, Springer-Verlag, London.*
Altschul, Methods in Enzymology, (1996), vol. 266, pp. 460-480.
Ashcroft et al., J. Clin. Pathol., (1988), vol. 41, pp. 467-470.
Barbas et al., Proc Nat. Acad. Sci, USA, (1994), vol. 91, pp. 3809-3813.
Carulli, M. et al., "Can CCL2 serum levels be used in risk stratification or to monitor treatment response in systemic sclerosis?", Ann Rheum Dis, (2008), vol. 67, pp. 105-109.
De Lau et al., J. Immunol., (1992), vol. 149, pp. 1840-1846.
Denton et al., Trends Immunol., (2005), vol. 26, No. 11, pp. 596-602.
Distler et al., Arthritis Rheum, (2001), vol. 44, No. 11, pp. 2665-2678.

(Continued)

*Primary Examiner* — Marianne P Allen
(74) *Attorney, Agent, or Firm* — Proskauer Rose LLP; Fangli Chen; Julio J. Mendez

(57) ABSTRACT

The present invention provides, among other things, bi-specific molecules including, but not limited to, antibodies, fynomers, aptamers, fusion proteins, and protein binding domains that bind both CCL2 and LOXL2 and uses thereof, in particular, for treatment of scleroderma and related fibrotic and/or inflammatory diseases, disorders and conditions. In some embodiments, the present invention further provides methods and compositions for treatment of scleroderma and related fibrotic and/or inflammatory diseases, disorders and conditions based on the combination of mono-specific anti-CCL2 and anti-LOXL2 molecules.

4 Claims, 13 Drawing Sheets
Specification includes a Sequence Listing.

(56) References Cited

OTHER PUBLICATIONS

Farina et al., "A Four-Gene Biomarker Predicts Skin Disease in Patients with Diffuse Cutaneous Systemic Sclerosis", Arthritis Rheum., (2010), vol. 62, No. 2, pp. 580-588.
Grabulovski et al., J Biol. Chem., (2007), vol. 282, pp. 3196-3204.
Hawkins et al., J. Mol. Biol., (1992), vol. 226, pp. 889-896.
Hoogenboom et al., Mol Immunol., (1991), vol. 28, No. 9, pp. 1027-1037.
Huston et al., Proc. Nat. Acad. Sci. USA, (1988), vol. 85, pp. 5879-5883.
Jackson et al., BR. J. Cancer, (1998), vol. 78, p. 181 188.
Jackson et al., J. Immunol., (1995), vol. 154, No. 7, pp. 3310-3319.
Koolwijk et al., Hybridoma, (1988), vol. 7, pp. 217-225.
Kreutz et al., J. Chromatography, (1998), vol. 14, pp. 161-170.
Larrick et al., Methods: A Companion to Methods in Enzymology, (1991), vol. 2, p. 106-110.
Lloyd et al., Exp Med., (1997), vol. 185, No. 7, pp. 1371-1380.
Loberg Robert D et al, "Targeting CCL2 with systemic delivery of neutralizing antibodies induces prostate cancer tumor regression in vivo", Cancer Research, American Association for Cancer Research, US, (2007), vol. 67, No. 19, pp. 9417-9424.
Lonberg et al., "Antigen-specific human antibodies from mice comprising four distinct genetic modifications", Nature, (1994), vol. 368, No. 6474, pp. 856-859.
Losman et al., Int. J. Cancer, (1990), vol. 46, p. 310.
Ludwicka-Bradley, A. et al., "Coagulation and autoimmunity in scleroderma interstitial lung disease", Semin Arthritis Rheum, (2011), vol. 41, No. 2, pp. 212-222.
Marks et al., "Bypassing immunization: building high affinity human antibodies by chain shuffling", Biotechnology (N Y, (1992), vol. 10, No. 7, pp. 779-783.
Marks et al., JMOL Biol., (1991), vol. 222, No. 3, pp. 581-597.
Matthew B. Greenblatt et al, "Interspecies Comparison of Human and Murine Scleroderma Reveals IL-13 and CCL2 as Disease Subset-Specific Targets", The American Journal of Pathology, (2012), vol. 180, No. 3, pp. 1080-1094.
Milano et al., "Molecular Subsets in the Gene Expression Signatures of Scleroderma Skin", PLOS ONE, (2008), vol. 3, No. 7, pp. 1-18.
Milstein; Cuello, Nature, (1983), vol. 305, No. 5934, pp. 537-540.
Osbourn et al., Immunotechnology, (1996), vol. 2, p. 181 196.
Reisfeld; Sell, Cancer Surv., (1985), vol. 4, No. 1, pp. 271-290.
Ridder et al., Biotechnology, (1995), vol. 13, p. 255-260.
Riechmann et al., Nature, (1988), vol. 332, No. 6162, pp. 323-327.
Sahin Hacer et al, "Chemokines in tissue fibrosis", Biochimica et Biophysica Acta. Molecular Basis of Disease, Amsterdam, NL, (2012), vol. 1832, pp. 1041-1048.
Schade et al., Altex, (1996), vol. 13, No. 5, pp. 80-85.
Schier et al., Gene, (1995), vol. 169, pp. 147-155.
Suresh et al., Proc. Natl. Acad. Sci. USA, (1986), vol. 83, pp. 7989-7993.
Vaughn et al., Nat. Biotechnol., (1996), vol. 14, pp. 309-314.
Verhoeyen et al., Science, (1988), vol. 239, No. 4847, pp. 1534-1536.
Vivian Barry-Hamilton et al, "Allosteric inhibition of lysyl oxidase-like-2 impedes the development of a pathologic microenvironment", Nature Medicine, (2010), vol. 16, No. 9, pp. 1009-1017.
Ward et al."Genetic Manipulation and Expression of Antibodies", Monoclonal Antibodies: Principles and Applications, Wiley-Liss, Inc., (1995), p. 137-185.
Yamamoto et al., J Dermatol Sci., (2001), vol. 26, No. 2, pp. 133-139.
Yamamoto T et al, "Role of cytokines in scleroderma: Use of animal models", Clinical and Applied Immunology Reviews, Elsevier, Amsterdam, NL, vol. 6, No. 1, (2006), pp. 1-19.
Yamamoto, T., "Scleroderma—Pathophysiology", Eur J Dermatol, vol. 19, No. 1, (2009), pp. 14-24.
Yelton et al., J. Immunol., (1995), vol. 155, pp. 1994-2004.
Zu-Yau Lin et al, "Cancer-associated fibroblasts up-regulate CCL2, CCL26, IL6 and LOXL2 genes related to promotion of cancer progression in hepatocellular carcinoma cells", Biomedicine & Pharmacotherapy, (2012), vol. 66, No. 7, pp. 525-529.

* cited by examiner

SEQUENCE LISTING

```
<160> NUMBER OF SEQ ID NOS: 2

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 638
<212> TYPE: PRT
<213> ORGANISM: Homo sapiens

<400> SEQUENCE: 2

Met Glu Gly Tyr Val Glu Val Lys Glu Gly Lys Thr Trp Lys Gln Ile
1               5                   10                  15

Cys Asp Lys His Trp Thr Ala Lys Asn Ser Arg Val Val Cys Gly Met
            20                  25                  30

Phe Gly Phe Pro Gly Glu Arg Thr Tyr Asn Thr Lys Val Tyr Lys Met
            35                  40                  45

Phe Ala Ser Arg Arg Lys Gln Arg Tyr Trp Pro Phe Ser Met Asp Cys
    50                  55                  60

Thr Gly Thr Glu Ala His Ile Ser Ser Cys Lys Leu Gly Pro Gln Val
65                  70                  75                  80

Ser Leu Asp Pro Met Lys Asn Val Thr Cys Glu Asn Gly Gln Pro Ala
                85                  90                  95

Val Val Ser Cys Val Pro Gly Gln Val Phe Ser Pro Asp Gly Pro Ser
```

```
              100                 105                 110
Arg Phe Arg Lys Ala Tyr Lys Pro Glu Gln Pro Leu Val Arg Leu Arg
            115                 120                 125
Gly Gly Ala Tyr Ile Gly Gly Arg Val Glu Val Leu Lys Asn Gly
            130                 135             140
Glu Trp Gly Thr Val Cys Asp Asp Lys Trp Asp Leu Val Ser Ala Ser
145                 150                 155                 160
Val Val Cys Arg Glu Leu Gly Phe Gly Ser Ala Lys Glu Ala Val Thr
                165                 170                 175
Gly Ser Arg Leu Gly Gln Gly Ile Gly Pro Ile His Leu Asn Glu Ile
            180                 185                 190
Gln Cys Thr Gly Asn Glu Lys Ser Ile Ile Asp Cys Lys Phe Asn Ala
            195                 200                 205
Glu Ser Gln Gly Cys Asn His Glu Glu Asp Ala Gly Val Arg Cys Asn
            210                 215                 220
Thr Pro Ala Met Gly Leu Gln Lys Lys Leu Arg Leu Asn Gly Gly Arg
225                 230                 235                 240
Asn Pro Tyr Glu Gly Arg Val Glu Val Leu Val Glu Arg Asn Gly Ser
                245                 250                 255
Leu Val Trp Gly Met Val Cys Gly Gln Asn Trp Gly Ile Val Glu Ala
                260                 265                 270
Met Val Val Cys Arg Gln Leu Gly Leu Gly Phe Ala Ser Asn Ala Phe
            275                 280                 285
Gln Glu Thr Trp Tyr Trp His Gly Asp Val Asn Ser Asn Lys Val Val
            290                 295                 300
Met Ser Gly Val Lys Cys Ser Gly Thr Glu Leu Ser Leu Ala His Cys
305                 310                 315                 320
Arg His Asp Gly Glu Asp Val Ala Cys Pro Gln Gly Gly Val Gln Tyr
                325                 330                 335
Gly Ala Gly Val Ala Cys Ser Glu Thr Ala Pro Asp Leu Val Leu Asn
                340                 345                 350
Ala Glu Met Val Gln Gln Thr Thr Tyr Leu Glu Asp Arg Pro Met Phe
            355                 360                 365
Met Leu Gln Cys Ala Met Glu Glu Asn Cys Leu Ser Ala Ser Ala Ala
            370                 375                 380
Gln Thr Asp Pro Thr Thr Gly Tyr Arg Arg Leu Leu Arg Phe Ser Ser
385                 390                 395                 400
Gln Ile His Asn Asn Gly Gln Ser Asp Phe Arg Pro Lys Asn Gly Arg
                405                 410                 415
His Ala Trp Ile Trp His Asp Cys His Arg His Tyr His Ser Met Glu
            420                 425                 430
Val Phe Thr His Tyr Asp Leu Leu Asn Leu Asn Gly Thr Lys Val Ala
            435                 440                 445
Glu Gly Gln Lys Ala Ser Phe Cys Leu Glu Asp Thr Glu Cys Glu Gly
            450                 455                 460
Asp Ile Gln Lys Asn Tyr Glu Cys Ala Asn Phe Gly Asp Gln Gly Ile
465                 470                 475                 480
Thr Met Gly Cys Trp Asp Met Tyr Arg His Asp Ile Cys Gln Trp
                485                 490                 495
Val Asp Ile Thr Asp Val Pro Pro Gly Asp Tyr Leu Phe Gln Val Val
                500                 505                 510
Ile Asn Pro Asn Phe Glu Val Ala Glu Ser Asp Tyr Ser Asn Asn Ile
            515                 520                 525
```

```
Met Lys Cys Arg Ser Arg Tyr Asp Gly His Arg Ile Trp Met Tyr Asn
    530                 535                 540

Ser His Ile Gly Gly Ser Phe Ser Glu Glu Thr Glu Lys Lys Phe Glu
545                 550                 555                 560

His Phe Ser Gly Leu Leu Asn Asn Gln Leu Ser Pro Pro Val Lys Lys
                565                 570                 575

Pro Ala Trp Ser Thr Pro Val Phe Arg Pro His His Ile Phe His Gly
                580                 585                 590

Thr Ser Pro Gln Gln Leu Ser Leu Asn Glu Cys His Val Pro Ser Pro
        595                 600                 605

Ser Pro Ala Pro Thr Leu Ser Arg Pro Leu Gln Leu Cys Leu Ser Ser
    610                 615                 620

Gly Gly Lys Gly Pro Ser His His Ser Trp Gly Ala Ala Thr
625                 630                 635
```

ANTI-CCL2 AND ANTI-LOXL2 COMBINATION THERAPY FOR TREATMENT OF SCLERODERMA

CROSS REFERENCE TO RELATED APPLICATIONS

This application is a 35 U.S.C. § 371 national stage filing of International Application No. PCT/US2014/039437, filed May 23, 2014, which claims priority to U.S. Provisional Patent Application No. 61/826,692, filed May 23, 2013, each of which is hereby incorporated by reference in its entirety.

SEQUENCE LISTING

The present specification makes reference to a Sequence Listing submitted in electronic form as an ASCII.txt file named "2006685-0569_ST25" on May 23, 2014. The .txt file was generated on May 12, 2014 and is 6751 bytes in size. The material contained in the text file is hereby incorporated by reference in its entirety.

BACKGROUND

Systemic sclerosis (scleroderma) is a clinically heterogeneous disorder of the connective tissue, resulting in hardening and tightening of the skin. It is an autoimmune-type of disease characterized by immune activation, vascular damage, and fibrosis. Major organ-based complications involving the lungs, heart, kidneys, and gastrointestinal tract can contribute to mortality and morbidity. The pathogenesis is unknown.

The feature most commonly associated with scleroderma is fibrosis—a buildup of collagen in the skin and organs. The buildup of collagen contributes to symptoms of the disorder, including hair loss, skin hardening and tightening, skin discoloration, joint pain, stiffness of fingers and joints, digestive tract problems and breathing complications (dry cough, shortness of breath, wheezing). Scleroderma may be classified into two major subgroups: limited cutaneous scleroderma and diffuse cutaneous scleroderma. In limited cutaneous scleroderma, fibrosis is mainly restricted to the hands, arms, and face. Diffuse cutaneous scleroderma is a rapidly progressing disorder that affects large areas of the skin and compromises one or more internal organs. Patients with limited cutaneous scleroderma have a relatively better long term prognosis than patients with diffuse cutaneous scleroderma. Widespread systemic scleroderma can damage the heart, kidney, lungs, or GI tract, which may cause death. Pulmonary fibrosis is the most common cause of death in patients with scleroderma.

Thus, scleroderma is an extremely debilitating disease with potentially fatal repercussions. There are about 50,000 patients in the US. The ratio of female patients to male patients is about 4:1. Current treatment methods are based only on symptomatic treatment and management of complications that arise through the course of the disease (e.g., corticosteroids, NSAIDs, and immune-suppressing medications such as Metotrexate and Cytoxan). There is no treatment shown to reverse or halt progression of disease. Therefore, there is a high unmet medical need for an effective treatment of scleroderma.

SUMMARY OF THE INVENTION

The present invention provides, among other things, improved methods and compositions for effective treatment of scleroderma, in particular, based on bi-specific binding molecules, including, but not limited to, antibodies, fynomers, aptamers, fusion proteins, protein binding domains (e.g., those derived from receptors) that can specifically bind to lysyl oxidase-like-2 ("LOXL2") and C—C chemokine ligand-2 ("CCL2"), and/or combination therapy based on such molecules that specifically bind to LOXL2 and CCL2. CCL2 is known to be a validated target for scleroderma. Several studies have shown that scleroderma fibroblasts display increased constitutive expression of CCL2 mRNA and protein. In scleroderma skin sections, expression of CCL2 was detected in fibroblasts, keratinocytes, and mononuclear cells, whereas it was undetectable in normal skin (Galindo et al., *Arthritis Rheum.* 2001 June; 44(6):1382-6; Distler et al., *Arthritis Rheum.* 2001 November; 44(11): 2665-78; Lioyd et al., *Exp Med.* 1997 Apr. 7; 185(7):1371-80; Yamamoto et al., *J Dermatol Sci.* 2001 Jun.; 26(2):133-9; Denton et al.; *Trends Immunol.* 2005 Nov.; 26(11):596-602. Epub 2005 Sep. 15.). However, prior to the present invention, no effective treatment for scleroderma has been developed based on anti-CCL2 antibodies. The present inventors observe that high levels of CCL2 in plasma sequester anti-CCL2 antibodies injected intravenously, resulting in wasted anti-CCL2 antibodies and ineffective targeting of CCL2 in diseased tissues. To solve this problem, the present inventors contemplate the use of bi-specific molecules that allow sequestering anti-CCL2 activity in diseased tissues with free anti-CCL2 arms that bind to tissue CCL2, which provides tissue specific targeting of CCL2. Thus, the present invention provides methods and compositions that preferentially inhibit tissue CCL2 as opposed to plasma CCL2, resulting in highly effective treatment of scleroderma.

Thus, in one aspect, the present invention provides bi-specific binding molecules (e.g., bi-specific antibodies, fynomers, aptamers, fusion proteins, or protein binding domains) comprising a first antigen-binding site that specifically binds to LOXL2 and a second antigen-binding site that specifically binds to CCL2.

In some embodiments, the first antigen-binding site specifically binds to LOXL2 with a binding affinity of 100 nM or greater (e.g., 10 nM or greater, 1 nM or greater, 500 pM or greater, 100 pM or greater, 50 pM or greater, 10 pM or greater, 1 pM or greater, 500 fM or greater, 400 fM or greater, 300 fM or greater, 200 fM or greater, 100 fM or greater, 50 fM or greater, 10 fM or greater, or 1 fM or greater).

In some embodiments, the second antigen-binding site specifically binds to CCL2 with a binding affinity of between about 500 nM and 1 fM (e.g., between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM). In some embodiments, the second antigen-binding site specifically binds to CCL2 with a binding affinity of greater than about 500 nM (e.g., greater than about 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM).

In some embodiments, the first antigen-binding site comprises a first full length heavy chain and a first full length light chain. In some embodiments, the first antigen-binding site comprises a first Fab fragment. In some embodiments, the first antigen-binding site comprises a first single-chain variable fragments (scFvs).

In some embodiments, the second antigen-binding site comprises a second full length heavy chain and a second full length light chain. In some embodiments, the second antigen-binding site comprises a second Fab fragment. In some embodiments, the second antigen-binding site comprises a second single-chain variable fragments (scFvs).

In some embodiments, the first and second antigen-binding sites are linked by a peptide linker. In some embodiments, the peptide linker is >5 (e.g., 6, 7, 8, 9, 10, 11, 12, 13, 14, 15, 20, 25 or more) amino acids long. In some embodiments, the first and second antigen binding sites are configured such that they form a single polypeptide chain.

In some embodiments, the first and second antigen-binding sites are associated via chemical cross-linking.

In some embodiments, a bi-specific binding molecule according to the invention is a bi-specific antibody. In some embodiments, the bi-specific antibody comprises an Fc region.

In some embodiments, the bi-specific antibody is human. In some embodiments, the bi-specific antibody is humanized.

In another aspect, the present invention provides pharmaceutical compositions comprising the bi-specific binding molecule (e.g., a bi-specific antibody, fynomer, aptamer, fusion protein, protein binding domain) as described herein and a pharmaceutically acceptable carrier.

In further aspect, the present invention provides methods of treating scleroderma comprising administering to an individual who is suffering from or susceptible to scleroderma a bi-specific binding molecule (e.g., a bi-specific antibody, fynomer, aptamer, fusion protein, protein binding domain) as described herein. In some embodiments, the bi-specific antibody is administered at a therapeutically effective dose and an administration interval such that at least one symptom or feature of scleroderma on a target tissue is reduced in intensity, severity, or frequency, or has delayed onset.

In some embodiments, the at least one pathological feature of scleroderma is ameliorated, including but not limited to, endothelial-cell damage, proliferation of basal-lamina layers, perivascular mononuclear-cell infiltration, fibrosis, derangement of visceral-organ architecture, rarefaction of blood vessels, hypoxia, and combination thereof.

In some embodiments, the target tissue is selected from the group consisting of skin, blood vessels, lung, heart, kidney, gastrointestinal tract (including liver), musculoskeletal system and combinations thereof. In some embodiments, the target tissue is lung. In some embodiments, the target tissue is heart.

In some embodiments, the individual is suffering from or susceptible to limited cutaneous scleroderma. In some embodiments, the individual is suffering from or susceptible to diffuse cutaneous scleroderma.

In some embodiments, the bi-specific antibody is administered parenterally. In some embodiments, the parenteral administration is selected from intravenous, intradermal, inhalation, transdermal (topical), subcutaneous, and/or transmucosal administration. In some embodiments, the parenteral administration is intravenous administration.

In some embodiments, the bi-specific antibody is administered orally.

In certain embodiments, the bi-specific antibody is administered bimonthly, monthly, triweekly, biweekly, weekly, daily, or at variable intervals.

In some embodiments, the bi-specific antibody is co-administered with one or more anti-fibrotic or anti-inflammatory agents.

In another aspect, the present invention provides use of a bi-specific binding molecule as described herein in the manufacture of a medicament for treatment of scleroderma, wherein the treatment comprises administering to an individual who is suffering from or susceptible to scleroderma an effective amount of the bi-specific molecule, wherein the bi-specific binding molecule comprises a first antigen-binding site that specifically binds to LOXL2 and a second antigen-binding site that specifically binds to CCL2

In some embodiments, the first antigen-binding site specifically binds to LOXL2 with a binding affinity of 100 nM or greater (e.g., 10 nM or greater, 1 nM or greater, 500 pM or greater, 100 pM or greater, 50 pM or greater, 10 pM or greater, 1 pM or greater, 500 fM or greater, 400 fM or greater, 300 fM or greater, 200 fM or greater, 100 fM or greater, 50 fM or greater, 10 fM or greater, or 1 fM or greater).

In some embodiments, the second antigen-binding site specifically binds to CCL2 with a binding affinity of between about 500 nM and 1 fM (e.g., between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM). In some embodiments, the second antigen-binding site specifically binds to CCL2 with a binding affinity of greater than about 500 nM (e.g., greater than about 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM).

In some embodiments, the first antigen-binding site comprises a first full length heavy chain and a first full length light chain. In some embodiments, the first antigen-binding site comprises a first Fab fragment. In some embodiments, the first antigen-binding site comprises a first single-chain variable fragments (scFvs).

In some embodiments, the second antigen-binding site comprises a second full length heavy chain and a second full length light chain. In some embodiments, the second antigen-binding site comprises a second Fab fragment. In some embodiments, the second antigen-binding site comprises a second single-chain variable fragments (scFvs).

In some embodiments, the first and second antigen-binding sites are linked by a peptide linker. In some embodiments, the peptide linker is >5 (e.g., 6, 7, 8, 9, 10, 11, 12, 13, 14, 15, 20, 25 or more) amino acids long. In some embodiments, the first and second antigen binding sites are configured such that they form a single polypeptide chain.

In some embodiments, the first and second antigen-binding sites are associated via chemical cross-linking.

In some embodiments, a bi-specific binding molecule according to the invention is a bi-specific antibody. In some embodiments, the bi-specific antibody comprises an Fc region.

In some embodiments, the bi-specific antibody is humanized.

In another aspect, the present invention provides a bi-specific binding molecule as described herein for use in a method of treating scleroderma comprising a step of administering an effective amount of the bi-specific binding molecule to a subject who is suffering from or susceptible to scleroderma, wherein the bi-specific binding molecule comprises a first antigen-binding site that specifically binds to LOXL2 and a second antigen-binding site that specifically binds to CCL2.

In some embodiments, the first antigen-binding site specifically binds to LOXL2 with a binding affinity of 100 nM or greater (e.g., 10 nM or greater, 1 nM or greater, 500 pM or greater, 100 pM or greater, 50 pM or greater, 10 pM or greater, 1 pM or greater, 500 fM or greater, 400 fM or greater, 300 fM or greater, 200 fM or greater, 100 fM or greater, 50 fM or greater, 10 fM or greater, or 1 fM or greater).

In some embodiments, the second antigen-binding site specifically binds to CCL2 with a binding affinity of between about 500 nM and 1 fM (e.g., between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM). In some embodiments, the second antigen-binding site specifically binds to CCL2 with a binding affinity of greater than about 500 nM (e.g., greater than about 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM).

In some embodiments, the first antigen-binding site comprises a first full length heavy chain and a first full length light chain. In some embodiments, the first antigen-binding site comprises a first Fab fragment. In some embodiments, the first antigen-binding site comprises a first single-chain variable fragments (scFvs).

In some embodiments, the second antigen-binding site comprises a second full length heavy chain and a second full length light chain. In some embodiments, the second antigen-binding site comprises a second Fab fragment. In some embodiments, the second antigen-binding site comprises a second single-chain variable fragments (scFvs).

In some embodiments, the first and second antigen-binding sites are linked by a peptide linker. In some embodiments, the peptide linker is >5 (e.g., 6, 7, 8, 9, 10, 11, 12, 13, 14, 15, 20, 25 or more) amino acids long. In some embodiments, the first and second antigen binding sites are configured such that they form a single polypeptide chain.

In some embodiments, the first and second antigen-binding sites are associated via chemical cross-linking.

In some embodiments, a bi-specific binding molecule according to the invention is a bi-specific antibody. In some embodiments, the bi-specific antibody comprises an Fc region.

In some embodiments, the bi-specific antibody is human. In some embodiments, the bi-specific antibody is humanized.

In yet another aspect, the present invention provides methods of treating fibrotic diseases, disorders or conditions comprising administering to an individual who is suffering from or susceptible to a fibrotic disease, disorder or condition a bi-specific binding molecule (e.g., a bi-specific antibody, fynomer, aptamer, fusion protein, protein binding domain) as described herein.

In another aspect, the present invention provides use of a bi-specific binding molecule as described herein in the manufacture of a medicament for treatment of fibrotic diseases, disorders or conditions, wherein the treatment comprises administering to an individual who is suffering from or susceptible to a fibrotic disease, disorder or condition the bi-specific binding molecule, wherein the bi-specific molecule comprises a first antigen-binding site that specifically binds to LOXL2 and a second antigen-binding site that specifically binds to CCL2.

In another aspect, the present invention provides a bi-specific molecule for use in a method of treating fibrotic diseases, disorders or conditions comprising a step of administering to an individual who is suffering from or susceptible to a fibrotic disease, disorder or condition the bi-specific binding molecule, wherein the bi-specific molecule comprises a first antigen-binding site that specifically binds to LOXL2 and a second antigen-binding site that specifically binds to CCL2.

In various embodiments, the fibrotic disease, disorder or condition is selected from the group consisting of skin fibrosis, kidney fibrosis, liver fibrosis, lung fibrosis, heart fibrosis, muscle fibrosis, and combination thereof.

In another aspect, the present invention provides methods of treating inflammatory diseases, disorders or conditions comprising administering to an individual who is suffering from or susceptible to an inflammatory disease, disorder or condition a bi-specific binding molecule as described herein.

In another aspect, the present invention provides use of a bi-specific binding molecule as described herein in the manufacture of a medicament for treatment of inflammatory diseases, disorders or conditions, wherein the treatment comprises administering to an individual who is suffering from or susceptible to an inflammatory diseases, disorders or condition the bi-specific binding molecule, wherein the bi-specific molecule comprises a first antigen-binding site that specifically binds to LOXL2 and a second antigen-binding site that specifically binds to CCL2.

In another aspect, the present invention provides a bi-specific molecule for use in a method of treating fibrotic diseases, disorders or conditions comprising a step of administering to an individual who is suffering from or susceptible to a fibrotic disease, disorder or condition the bi-specific binding molecule, wherein the bi-specific molecule comprises a first antigen-binding site that specifically binds to LOXL2 and a second antigen-binding site that specifically binds to CCL2.

In various embodiments, the inflammatory disease, disorder or condition is selected from the group consisting of psoriasis, rheumatoid arthritis, atherosclerosis, epilepsy, Alzheimer's disease, obesity, lupus nephritis, general kidney inflammation, multiple sclerosis, Crohn's disease, asthma, discoid lupus erythematosus, inflammatory bowel disease, or systemic lupus erythematosus.

In another aspect, the present invention provides methods of treating scleroderma comprising administering to an individual who is suffering from or susceptible to scleroderma an anti-CCL2 antibody, or fragment thereof, and an anti-LOXL2 antibody, or fragment thereof.

In another aspect, the present invention provides use of an anti-CCL2 antibody, or fragment thereof, and an anti-LOXL2 antibody, or fragment thereof, in the manufacture of a medicament for treatment of scleroderma, wherein the treatment comprises a step of administering the anti-CCL2 antibody, or fragment thereof, and the anti-LOXL2 antibody, or fragment thereof, to an individual who is suffering from or susceptible to scleroderma.

In another aspect, the present invention provides an anti-CCL2 antibody, or fragment thereof, and an anti-LOXL2 antibody, or fragment thereof, for use in a method of treating scleroderma comprising a step of administering the anti-CCL2 antibody, or fragment thereof, and the anti-LOXL2 antibody, or fragment thereof, to an individual who is suffering from or susceptible to scleroderma.

In some embodiments, the anti-CCL2 antibody, or fragment thereof, and the anti-LOXL2 antibody, or fragment thereof, are administered simultaneously. In some embodiments, the anti-CCL2 antibody, or fragment thereof, and the anti-LOXL2 antibody, or fragment thereof, are administered sequentially.

In some embodiments, the anti-CCL2 antibody, or fragment thereof, has a binding affinity of 1 nM or greater (e.g., 500 pM or greater, 100 pM or greater, 50 pM or greater, 10 pM or greater, 1 pM or greater, 500 fM or greater, 400 fM or greater, 300 fM or greater, 200 fM or greater, 100 fM or greater, 50 fM or greater, 10 fM or greater, 1 fM or greater).

In some embodiments, the anti-LOXL2 antibody, or fragment thereof, has a binding affinity of 1 pM or greater (e.g., 500 fM or greater, 400 fM or greater, 300 fM or greater, 200 fM or greater, 100 fM or greater, 50 fM or greater, 10 fM or greater, 1 fM or greater).

In some embodiments, the anti-CCL2 antibody, or fragment thereof, is selected from the group consisting of intact IgG, F(ab')2, F(ab)2, Fab', Fab, ScFvs, diabodies, triabodies and tetrabodies.

In some embodiments, the anti-LOXL2 antibody, or fragment thereof, is selected from the group consisting of intact IgG, F(ab')2, F(ab)2, Fab', Fab, ScFvs, diabodies, triabodies and tetrabodies.

In some embodiments, one or both of the anti-CCL2 antibody, or fragment thereof, and the anti-LOXL2 antibody, or fragment thereof, are humanized.

In some embodiments, the anti-CCL2 antibody, or fragment thereof, and the anti-LOXL2 antibody, or fragment thereof, are administered via same administration route. In some embodiments, the anti-CCL2 antibody, or fragment thereof, and the anti-LOXL2 antibody, or fragment thereof, are administered via different administration route.

In some embodiments, the anti-CCL2 antibody, or fragment, is administered intravenously, intradermally, by inhalation, transdermally (topically), subcutaneously, transmucosally, and/or orally.

In some embodiments, the anti-CCL2 antibody, or fragment thereof, is administered bimonthly, monthly, triweekly, biweekly, weekly, daily, or at variable intervals.

In some embodiments, the anti-LOXL2 antibody, or fragment, is administered intravenously, intradermally, by inhalation, transdermally (topically), subcutaneously, transmucosally, and/or orally.

In some embodiments, the anti-LOXL2 antibody, or fragment thereof, is administered bimonthly, monthly, triweekly, biweekly, weekly, daily, or at variable intervals.

In another aspect, the present invention provides methods of treating fibrotic diseases, disorders or conditions comprising administering to an individual who is suffering from or susceptible to a fibrotic disease, disorder or condition an anti-CCL2 antibody, or fragment thereof, and an anti-LOXL2 antibody, or fragment thereof.

In another aspect, the present invention provides use of an anti-CCL2 antibody, or fragment thereof, and an anti-LOXL2 antibody, or fragment thereof, in the manufacture of a medicament for treatment of fibrotic diseases, disorders or conditions, wherein the treatment comprises a step of administering the anti-CCL2 antibody, or fragment thereof, and the anti-LOXL2 antibody, or fragment thereof, to an individual who is suffering from or susceptible to a fibrotic disease, disorder or condition.

In another aspect, the present invention provides an anti-CCL2 antibody, or fragment thereof, and an anti-LOXL2 antibody, or fragment thereof, for use in a method of treating fibrotic diseases, disorders or conditions comprising a step of administering the anti-CCL2 antibody, or fragment thereof, and the anti-LOXL2 antibody, or fragment thereof, to an individual who is suffering from or susceptible to a fibrotic disease, disorder or condition.

In another aspect, the present invention provides methods of treating inflammatory diseases, disorders or conditions comprising administering to an individual who is suffering from or susceptible to an inflammatory disease, disorder or condition an anti-CCL2 antibody, or fragment thereof, and an anti-LOXL2 antibody, or fragment thereof.

In another aspect, the present invention provides use of an anti-CCL2 antibody, or fragment thereof, and an anti-LOXL2 antibody, or fragment thereof, in the manufacture of a medicament for treatment of inflammatory diseases, disorders or conditions, wherein the treatment comprises a step of administering the anti-CCL2 antibody, or fragment thereof, and the anti-LOXL2 antibody, or fragment thereof, to an individual who is suffering from or susceptible to an inflammatory disease, disorder or condition.

In another aspect, the present invention provides an anti-CCL2 antibody, or fragment thereof, and an anti-LOXL2 antibody, or fragment thereof, for use in a method of treating inflammatory diseases, disorders or conditions comprising a step of administering the anti-CCL2 antibody, or fragment thereof, and the anti-LOXL2 antibody, or fragment thereof, to an individual who is suffering from or susceptible to an inflammatory disease, disorder or condition.

In another aspect, the present disclosure provides kits comprising an anti-CCL2 antibody, or fragment thereof, and an anti-LOXL2 antibody, or fragment thereof.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The Drawing included herein, which is comprised of the following Figures, is for illustration purposes only not for limitation.

DEFINITIONS

Figure 1:
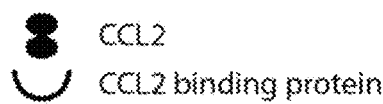
FIGS. 1A-1F illustrate diagrams depicting exemplary anti-CCL2 and anti-LOXL2 bi-specific antibodies.
Figure 1:
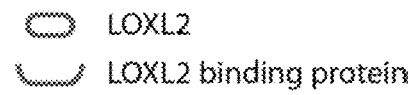
Figure 1:
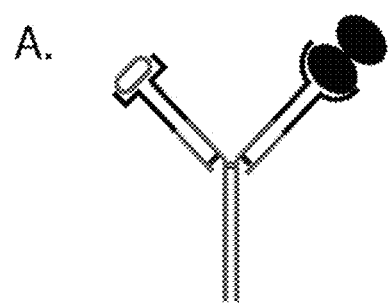
Figure 1:
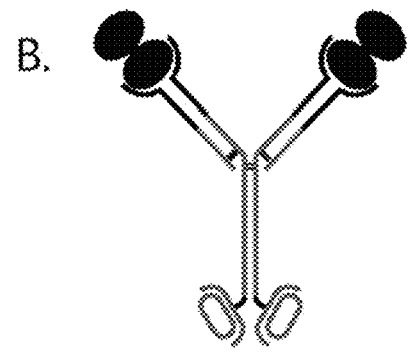
Figure 1:
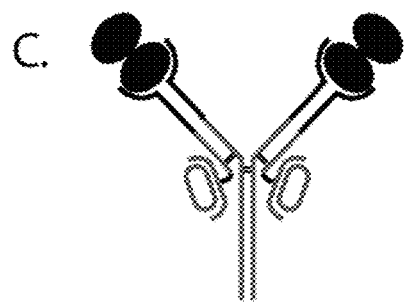
Figure 1:
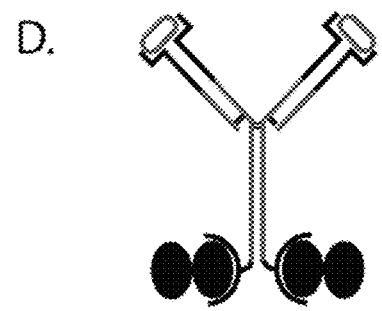
Figure 1:
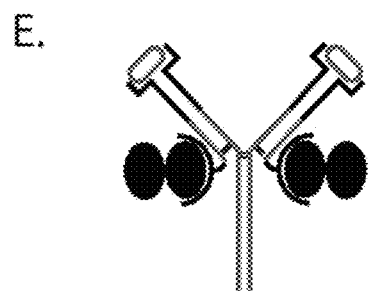
Figure 1:
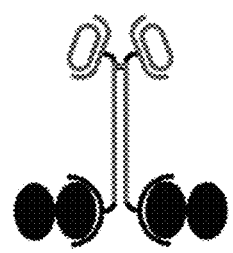

In order for the present invention to be more readily understood, certain terms are first defined. Additional definitions for the following terms and other terms are set forth throughout the specification.

Affinity: As is known in the art, "affinity" is a measure of the tightness with which a particular ligand binds to (e.g., associates non-covalently with) and/or the rate or frequency with which it dissociates from, its partner. As is known in the art, any of a variety of technologies can be utilized to determine affinity. In many embodiments, affinity represents a measure of specific binding.

Affinity-matured (or affinity-matured antibody): As used herein, refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al. Bio-Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7): 3310-9 (1995); and Hawkins et al, J. Mol. Biol. 226:889-896 (1992).

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer to these light and heavy chains respectively. An antibody can be specific for a particular antigen. The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked $V_H$::$V_L$ heterodimer which may be expressed from a nucleic acid including $V_H$- and $V_L$-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding agent: As used herein, the term "binding agent" includes any naturally occurring, synthetic or genetically engineered agent, such as protein, that binds an antigen or a target protein or peptide. "Binding agent" is also referred to as "binding protein." Binding agents can be derived from naturally occurring antibodies or synthetically engineered. A binding protein or agent can function similarly to an antibody by binding to a specific antigen to form a complex and elicit a biological response (e.g., agonize or antagonize a particular biological activity). Binding agents or proteins can include isolated fragments, "Fv" fragments consisting of the variable regions of the heavy and light chains of an antibody, recombinant single chain polypeptide molecules in which light and heavy chain variable regions are connected by a peptide linker ("ScFv proteins"), and minimal recognition units consisting of the amino acid residues that mimic the hypervariable region. The term Binding Agent as used herein can also include antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778. In some embodiments, the term Binding Agent as used herein can also include antibody. See the definition of Antibody.

Bi-specific: The term "bi-specific" as used herein refers to a molecule having two distinct binding specificities. Typically, a bi-specific binding molecule contains at least two antigen-binding sites, each of which specifically binds to a different antigen or epitope. A bi-specific molecule can be, for example, a bi-specific antibody, fynomer, aptamer, fusion protein, protein binding domain. As used herein, bi-specific molecules encompass molecules (e.g., antibodies, fynomers, aptamers, fusion proteins, protein binding domains or other binding agents) having higher valencies (i.e., the ability to bind more than two antigens, or epitopes), which are also referred to as multispecific molecules.

Bispecific antibody: The term "bispecific antibody" as used herein, refers to a bispecific binding molecule in which at least one, and typically both, of the binding moieties is or comprises an antibody component or fragment. A variety of different bi-specific antibody structures is known in the art. In some embodiments, each binding moiety in a bispecific antibody that is or comprises an antibody component or fragment includes $V_H$ and/or $V_L$ regions; in some such embodiments, the $V_H$ and/or $V_L$ regions are those found in a particular monoclonal antibody. In some embodiments, where the bispecific antibody contains two antibody component binding moieties, each includes $V_H$ and/or $V_L$ regions from different monoclonal antibodies.

Bispecific binding molecule: The term "bispecific binding molecule" as used herein, refers to a polypeptide with two discrete binding moieties, each of which binds with a distinct target. In some embodiments, a bispecific binding molecule is a single polypeptide; in some embodiments, a bispecific binding molecule is or comprises a plurality of peptides which, in some such embodiments may be covalently associated with one another, for example by cross-linking. In some embodiments, the two binding moieties of a bispecific binding molecule recognize different sites (e.g., epitopes) the same target (e.g., antigen); in some embodiments, they recognize different targets. In some embodiments, a bispecific binding molecule is capable of binding simultaneously to two targets which are of different structure.

CDR: The term "CDR" as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Boundaries of CDRs have been defined differently depending on the system, of which several are known in the art (e.g., Kabat, Chothia, etc.).

Chimeric: A "chimeric" antibody as used herein, is a recombinant protein that contains the variable domains including the complementarity-determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

Combination: The term "in combination" as used herein, refers to the use of more than one prophylactic and/or therapeutic agents (e.g., an anti-CCL2 antibody and an anti-LOXL2 antibody). The use of the term "in combination" does not restrict the order in which prophylactic and/or therapeutic agents are administered to a subject with a disorder. A first prophylactic or therapeutic agent (e.g., an anti-CCL2 antibody) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent (e.g., an anti-LOXL2 antibody) to a subject with a disorder.

Compound and Agent: The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule or a mixture or complex of at least two molecules.

Comparable: The term "comparable" as used herein, refers to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Diagnosis: As used herein, the term "diagnosis" refers to a process aimed at determining if an individual is afflicted with a disease or ailment. In the context of the present invention, "diagnosis of scleroderma" refers to a process aimed at one or more of: determining if an individual is afflicted with scleroderma, identifying a scleroderma subtype (i.e., diffuse or limited cutaneous scleroderma), and determining the severity of the disease.

Effective amount: As used herein, the term "effective amount" refers to an amount of a compound or agent that is sufficient to fulfill its intended purpose(s). In the context of the present invention, the purpose(s) may be, for example: to modulate the cause or symptoms of scleroderma; and/or to delay or prevent the onset of scleroderma; and/or to slow down or stop the progression, aggravation, or deterioration of the symptoms of scleroderma; and/or to alleviate one or more symptoms associated with scleroderma; and/or to bring about amelioration of the symptoms of scleroderma, and/or to cure scleroderma.

Framework or framework region: As used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

Human antibody: As used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Humanized: As is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $CH_1$, hinge, $CH_2$, $CH_3$, and, optionally, a $CH_4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

Fynomers: As used herein, the term "fynomers" refers to a class of binding proteins derived from the Src homology (SH3) domain of the human Fyn kinase, which is a human protein composed of 63 amino acid residues (D. Grabulovski et al. J. Biol. Chem. 282, 3196-3204 (2007)). Fynomers can bind to target molecules with the same affinity and specificity as antibodies. It can be produced in bacteria with high yields. Moreover, several Fynomers can be linked to yield a protein with multiple binding specificities Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same type and approximately the same severity of scleroderma as the individual being treated, who is about the same age as the individual being treated (to ensure that the stages of the disease in the treated individual and the control individual(s) are comparable).

Kit: As used herein, the term "kit" refers to any delivery system for delivering materials. Such delivery systems may include systems that allow for the storage, transport, or delivery of various diagnostic or therapeutic reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contain a subportion of the total kit components are included in the term "fragmented kit." In contrast, a "combined kit" refers to a delivery system containing all of the components in a single container (e.g., in a single box housing each of the desired components). The term "kit" includes both fragmented and combined kits.

Normal: As used herein, the term "normal," when used to modify the term "individual" or "subject" refers to an individual or group of individuals who does not have a particular disease or condition and is also not a carrier of the disease or condition. The term "normal" is also used herein to qualify a biological specimen or sample isolated from a normal or wild-type individual or subject, for example, a "normal biological sample."

Nucleic Acid: As used herein the term "nucleic acid" refers to an oligonucleotide, nucleotide or polynucleotide, and fragments or portions thereof, and to DNA or RNA of genomic or synthetic origin that may be single or double stranded, and represents the sense or antisense strand.

Nucleic Acid Molecule: The terms "nucleic acid molecule" and "polynucleotide" are used herein interchangeably. They refer to a deoxyribonucleotide or ribonucleotide polymer in either single- or double-stranded form, and unless otherwise stated, encompass known analogs of natural nucleotides that can function in a similar manner as naturally occurring nucleotides. The terms encompasses nucleic acid-like structures with synthetic backbones, as well as amplification products.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sample: As used herein, the term "sample" encompasses any sample obtained from a biological source. The terms "biological sample" and "sample" are used interchangeably. A biological sample can, by way of non-limiting example, include skin tissue, liver tissue, kidney tissue, lung tissue, cerebrospinal fluid (CSF), blood, amniotic fluid, sera, urine, feces, epidermal sample, skin sample, cheek swab, sperm, amniotic fluid, cultured cells, bone marrow sample and/or chorionic villi. Cell cultures of any biological samples can also be used as biological samples. A biological sample can also be, e.g., a sample obtained from any organ or tissue (including a biopsy or autopsy specimen), can comprise cells (whether primary cells or cultured cells), medium conditioned by any cell, tissue or organ, tissue culture. In some embodiments, biological samples suitable for the invention are samples which have been processed to release or otherwise make available a nucleic acid for detection as described herein. Fixed or frozen tissues also may be used.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Suffering from: An individual who is "suffering from" a disease, disorder, and/or condition (e.g., scleroderma) has been diagnosed with or displays one or more symptoms of the disease, disorder, and/or condition.

Susceptible to: An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, scleroderma) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, and/or condition; (5) a family history of the disease, disorder, and/or condition; (6) reaction to certain bacteria or viruses; (7) exposure to certain chemicals. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Treatment: As used herein, the term "treatment" (also "treat" or "treating") refers to any administration of a therapeutic molecule (e.g., bi-specific anti-CCL2/LOXL antibody or simultaneous or sequential co-administration of an anti-CCL2 monoclonal antibody or antigen binding fragment thereof and an anti-LOXL2 monoclonal antibody or antigen binding fragment thereof) that partially or completely alleviates, ameliorates, relieves, inhibits, delays onset of, reduces severity of and/or reduces incidence of one or more symptoms or features of a particular disease, disorder, and/or condition (e.g., scleroderma, fibrosis or inflammation). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION OF THE INVENTION

The present invention provides, among other things, bi-specific molecules, including including, but not limited to, antibodies, fynomers, aptamers, fusion proteins, protein binding domains (e.g., those derived from receptors) against CCL2 and LOXL2 and uses thereof, in particular, for treatment of scleroderma and related fibrotic and/or inflammatory diseases, disorders and conditions. In some embodiments, the present invention further provides methods and compositions for treatment of scleroderma and related fibrotic and/or inflammatory diseases, disorders and conditions based on the combination of mono-specific anti-CCL2 and anti-LOXL2 molecules (e.g., antibodies).

The present invention is, in part, based on the unique insights observed by the present inventors, that is, bi-specific molecules, including antibodies or fusion proteins, allow tissue specific targeting of CCL2 without wasting anti-CCL2 molecules such as antibodies in plasma, resulting in highly effective treatment of scleroderma. Embodiments of the invention include bi-specific antibodies that bind to both CCL2 and LOXL2. Bi-specific antibodies capable of binding to CCL2 and LOXL2 are particularly advantageous in that they possess a unique tissue selectivity profile and have the potential to arrest and clear development of scleroderma, fibrosis and inflammation. As LOXL2 is an important enzyme for the development of connective tissue, anti-LOXL2 binding activity may be used to preferentially target or identify tissues with relatively large amounts of connective tissue. Likewise, anti-LOXL2 binding activity may be used to target or identify tissues with aberrant connective tissue formation; e.g., as may be observed in scleroderma. Moreover, an anti-LOXL2 antibody provides synergistic therapeutic benefit in that inhibition or neutralization of LOXL2 reduces amine oxidase activity afflicted tissues, thus blocking an initiating step in the formation of connective tissue. The therapeutic benefit and tissue specificity of LOXL2 antibodies can be combined with the therapeutic efficacy of a neutralizing anti-CCL2 monoclonal antibody to synergistically target inflammation and reduce fibrotic formation. This synergistic targeting is particularly important in the treatment of more advanced cases of scleroderma because the LOX binding allows anti-CCL2 antibodies to be sequestered and compensates for decreased permeability due to fibrosis.

Various aspects of the invention are described in detail in the following sections. The use of sections is not meant to limit the invention. Each section can apply to any aspect of the invention. In this application, the use of "or" means "and/or" unless stated otherwise.

Scleroderma

Scleroderma, or systemic sclerosis, is generally considered a chronic systemic autoimmune disease characterized, among other things, fibrosis or hardening, vascular alterations, and autoantibodies. Without wishing to be bound by theory, it is thought that scleroderma is caused by a hyperactive autoimmune response trapped in a reinforcing amplification loop. For example, scleroderma is histologically characterized by inflammatory infiltrates of mononuclear cells, which in turn activate and are associated with increased collagen synthesis in the surrounding fibroblasts. In particular, activated macrophages produce TGF-beta and PDGF, which activate fibroblasts in the affected areas to produce high amounts of collagen.

T cells also appear to play a role in the disease process through activation of macrophages and the direct release of inflammatory pro-fibrogenic cytokines. In addition to collagen, the activated fibroblasts appear to secrete factors that recruit additional inflammatory cells to the affected areas, which release cytokines, which recruit further cytokine-releasing inflammatory cells, thereby leading to unregulated inflammation and tissue fibrosis.

Typically, monocytes/macrophages and T cells increase in both numbers and activation in the circulation and tissues of scleroderma patients. Tissue accumulation is both a cause and effect of microvascular injury, which is one of the early events in the pathogenesis of scleroderma. The microvascular injury is characterized by endothelial-cell damage, the proliferation of basal-lamina layers, occasional entrapment of peripheral-blood mononuclear cells in the vessel wall, and initial perivascular mononuclear-cell infiltrates. As the inflammatory cascades worsen, it is dominated by fibrosis, derangement of visceral organ architecture, rarefaction of blood vessels, and consequently, hypoxia. All of these factors and the continual recruitment of monocytes contributes to the maintenance of fibrosis In some embodiments, scleroderma is also considered a connective tissue disease generally characterized with an excessive accumulation of Extracellular Matrix proteins in the skin and internal organs, vascular injury, and immunological abnormalities.

Many of the clinical manifestations of the disease are thought to involve a misregulation of vascular remodeling. One of the earliest symptoms of scleroderma is microvascular injury. This microvascular injury is thought to cause increased endothelial cell activation. Activated endothelial cells are believed to express adhesion molecules resulting in altered capillary permeability allowing migration of inflammatory cells through the endothelium and entrapment in the vessel wall. The immune activation is thought to contribute to sustained endothelial activation, which results in the breakdown of endothelial cells. This process is believed to contribute to the loss of elasticity and narrowing of the vessels commonly observed in scleroderma patients. Furthermore, it is thought that microvascular injury contributes to perivascular infiltrates of mononuclear cells in the dermis which is thought to contribute to the activation of fibroblasts and may of the associated hallmark symptoms of scleroderma.

Many of the clinical manifestations of the disease are generally thought to involve the misregulation of fibroblasts. The main function of fibroblasts is to maintain the structural integrity of connective tissues by continuously secreting precursors of the extracellular matrix. Fibroblasts provide a structural framework (stroma) for many tissues, play an important role in wound healing and are the most common cells of connective tissue in animals. Fibroblasts are morphologically heterogeneous with diverse appearances depending on their location and activity.

There are two major forms of scleroderma: limited systemic sclerosis/scleroderma and diffuse systemic sclerosis/scleroderma. In limited cutaneous scleroderma, the fibrosis of the skin is generally confined to the area proximal to the elbow. Patients with limited cutaneous scleroderma generally experience vascular impairment. Cutaneous and organ fibrosis generally progresses slowly in patients with limited scleroderma. Patients with diffuse scleroderma generally experience fibrosis of skin and organs that progresses more rapidly than in limited scleroderma and/or widespread inflammation and/or more severe internal organ involvement than is seen in limited scleroderma.

It is generally thought that interstitial lung disease, resulting in pulmonary fibrosis, is the leading cause of scleroderma related deaths (Ludwicka-Bradley, A., et al. Coagulation and autoimmunity in scleroderma interstitial lung disease. Semin Arthritis Rheum, 41(2), 212-22, 2011). Further complications resulting in scleroderma-related deaths include but are not limited to cancer, heart failure, pulmonary hypertension, kidney failure, and malabsorption, or any combination thereof.

Scleroderma is most commonly diagnosed by inspection of skin symptoms. Tests to diagnosis include but are not limited to visual and/or manual inspection of the skin, blood pressure testing, chest x-ray, lung CT, echocardiogram, urinalysis, skin biopsy, and blood tests including antinuclear antibody testing, antitopoisomerase antibody testing, anti-centromere antibody testing, anti-U3 antibody testing, anti-RNA antibody testing, other types of antibody testing, erythrocyte sedimentation rate, and rheumatoid factor.

Bi-Specific Anti-CCL2 and Anti-LOXL2 Molecules

The present invention provides methods and compositions for treating scleroderma, and related fibrotic and/or inflammatory diseases, disorders and conditions based on administration of molecules that bind both CCL2 and LOXL2, in particular, bi-specific anti-CCL2 and LOXL2 molecules. In some embodiments, bi-specific molecules are nucleic acids, such as, bi-specific nucleic acid aptamers. In some embodiments, bi-specific molecules are proteins, such as, bi-specific fusion proteins, protein aptamers, and protein binding domains. In some embodiments, bi-specific molecules comprise bi-specific fynomers. In some embodiments, bi-specific molecules comprise bi-specific antibodies. In some embodiments, a bi-specific antibody suitable for the present invention includes a first antigen-binding site that specifically binds to LOXL2 and a second antigen-binding site that specifically binds to CCL2 (see FIG. 1).

CCL2

CCL2 is a chemokine produced by a variety of cell types. It is also known as monocyte chemoattractant protein-1 (MCP-1). CCL2 is known to be a potent attractant for many cell types of the immune system, including but not limited to monocytes, CD4 and CD8 memory T lymphocytes and NK cells (Carulli, M. et al. Can CCL2 serum levels be used in risk stratification or to monitor treatment response in systemic sclerosis? Ann Rheum Dis, 67, 105-109, 2008, Yamamoto, T. Scleroderma—Pathophysiology. Eur J Dermatol, 19 (1), 14-24). CCL2 has been shown to promote leukocyte migration across endothelial monolayers, suggesting a role in the promotion of perivascular infiltrates of mononuclear cells (Id.). CCL2 has also been shown to promote activation of fibroblasts and to upregulate Collagen type I mRNA expression in rat fibroblasts in vitro. Elevated CCL2 levels have been shown in patients with scleroderma and also in animal models of scleroderma (Id.). Specifically, increased CCL2 expression levels have been shown in scleroderma skin and increased CCL2 RNA and protein has been shown in scleroderma fibroblasts (Id.).

Human CCL2 is an 8.6 kDa protein containing 76 amino acid residues, the amino acid sequence of which is shown in Table 1. It is expressed by a variety of cell types, including monocytes, vascular endothelial cells, smooth muscle cells, certain epithelial cells, among others and binds its receptor CCR2. CCL2 belongs to the family of the CC chemokines which contains two cysteine residues that are adjacent (the adjacent cysteine residues underlined in Table 1).

TABLE 1

| | |
|---|---|
| Human CCL2 Protein Sequence (GeneBank: NP_002973) | MKVSAALLCLLLIAATFIPQGLAQPDAINAPVT<u>CC</u>YNFT NRKISVQRLASYRRITSSKCPKEAVIFKTIVAKEICADP KQKWVQDSMDHLDKQTQTPKT (SEQ ID NO: 1) |

CCL2 has also been purified, characterized, cloned and sequenced from non-human sources and can be recombinantly produced or chemically synthesized. As used herein, the term CCL2 encompasses any CCL2 proteins naturally-occurring in other species including, but not limited to, mouse, rats, primates, pigs, chickens, dogs, goats, cheeps, horses, camels, llama, to name but a few, and any recombinant or synthetic CCL2 that is substantially homologous or identical to human CCL2. In some embodiments, a CCL2 protein as used herein has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a CCL2 protein as used herein has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. Typically, a CCL2 protein substantially homologous or identical to human CCL2 also retains substantial activity of human CCL2.

Any of the above described CCL2 proteins can be used to generate and identify mono-specific and/or bi-specific antibodies that specifically bind to CCL2. See the Anti-CCL2 Antibodies and Bi-specific Anti-CCL2 and LOXL2 Antibodies sections below.

LOXL2

LOXL2 is a member of the lysyl oxidase family of copper-dependent amine oxidases. Without wishing to be bound by theory, it is thought that LOXL2 catalyzes the covalent cross-link of the component side chains of collagen and those of elastin, thus stabilizing these proteins in the extracellular matrix (ECM). The polypeptide sequence of human LOXL2 is well characterized, as shown in Table 2.

TABLE 2

| | |
|---|---|
| Human LOXL2 Protein Sequence (GeneBank: AAD34343) | MEGYVEVKEGKTWKQICDKHWTAKNSRVVCGMFGFPG ERTYNTKVYKMFASRRKQRYWPFSMDCTGTEAHISSC KLGPQVSLDPMKNVTCENGQPAVVSCVPGQVFSPDGP SRFRKAYKPEQPLVRLRGGAYIGEGRVEVLKNGEWGT VCDDKWDLVSASVVCRELGFGSAKEAVTGSRLGQGIG PIHLNEIQCTGNEKSIIDCKFNAESQGCNHEEDAGVR CNTPAMGLQKKLRLNGGRNPYEGRVEVLVERNGSLVW GMVCGQNWGIVEAMVVCRQLGLGFASNAFQETWYWHG DVNSNKVVMSGVKCSGTELSLAHCRHDGEDVACPQGG VQYGAGVACSETAPDLVLNAEMVQQTTYLEDRPMFML QCAMEENCLSASAAQTDPTTGYRRLLRFSSQIHNNGQ SDFRPKNGRHAWIWHDCRHRYHSMEVFTHYDLLNLNG TKVAEGQKASFCLEDTECEGDIQKNYECANFGDQGIT MGCWDMYRHDIDCQWVDITDVPPGDYLFQVVINPNFE VAESDYSNNIMKCRSRYDGHRIWMYNSHIGGSFSEET EKKFEHFSGLLNNQLSPPVKKPAWSTPVFRPHHIFHG TSPQQLSLNECHVPSPSPAPTLSRPLQLCLSSGGKGP SHHSWGAAT (SEQ ID NO: 2) |

LOXL2 has also been purified, characterized, cloned and sequenced from non-human sources and can be recombinantly produced or chemically synthesized. As used herein, the term LOXL2 encompasses any LOXL2 proteins naturally-occurring in other species including, but not limited to, mouse, rats, primates, pigs, chickens, dogs, goats, cheeps, horses, camels, llama, to name but a few, and any recombinant or synthetic LOXL2 that is substantially homologous or identical to human LOXL2. In some embodiments, a LOXL2 protein as used herein has a sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a LOXL2 protein as used herein has a sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. Typically, a LOXL2 protein substantially homologous or identical to human LOXL2 also retains substantial activity of human LOXL2.

Any of the above described LOXL2 proteins can be used to generate and identify desired mono-specific and/or bi-specific antibodies that specifically bind to LOXL2. See the Anti-LOXL2 Antibodies and Bi-specific Anti-CCL2 and LOXL2 Antibodies sections below.

"Percent (%) amino acid sequence identity" with respect to the CCL2 and LOXL2 sequences identified herein is defined as the percentage of amino acid residues in a candidate sequence that are identical with the amino acid residues in the CCL2 or LOXL2 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above.

Anti-CCL2 and Anti-LOXL2 Mono-Specific Antibodies

CCL2 and LOXL2 proteins described herein, or fragments thereof, can be used to generate antibodies by methods well known to those of skill in the art. As used herein, anti-CCL2 mono-specific antibodies include any antibodies or fragments of antibodies that bind specifically to any epitopes of CCL2 and anti-LOXL2 mono-specific antibodies include any antibodies or fragments of antibodies that bind specifically to any epitopes of LOXL2. As used herein, the term "antibodies" is intended to include immunoglobulins and fragments thereof which are specifically reactive to the designated protein or peptide, or fragments thereof. For example, the term "antibodies" includes intact monoclonal antibodies, polyclonal antibodies, single domain antibodies (e.g., shark single domain antibodies (e.g., IgNAR or fragments thereof)), and antibody fragments so long as they exhibit the desired biological activity. Suitable antibodies also include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), and antibody fragments.

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Mono-specific antibodies can be generated using methods well known in the art. For example, protocols for antibody production are described by Harlow and Lane, Antibodies: A Laboratory Manual, (1988). Typically, antibodies can be generated in mouse, rat, guinea pig, hamster, camel, llama, shark, or other appropriate host. Alternatively, antibodies may be made in chickens, producing IgY molecules (Schade et al., (1996) *ALTEX* 13(5):80-85). In some embodiments, antibodies suitable for the present invention are subhuman primate antibodies. For example, general techniques for raising therapeutically useful antibodies in baboons may be found, for example, in Goldenberg et al., international patent publication No. WO 91/11465 (1991), and in Losman et al., *Int. J. Cancer* 46: 310 (1990). In some embodiments, monoclonal antibodies may be prepared using hybridoma methods (Milstein and Cuello, (1983) Nature 305(5934): 537-40.). In some embodiments, monoclonal antibodies may also be made by recombinant methods (U.S. Pat. No. 4,166,452, 1979).

Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must typically contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., Nat. Biotechnol., 14: 309 314

(1996). An scFv library with a large repertoire can be constructed by isolating V-genes from non-immunized human donors using PCR primers corresponding to all known $V_H$, $V_k$ and $V_\lambda$ gene families. Following amplification, the $V_k$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the JH region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., Biotechnology, 13: 255 260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181 188 (1998); Osbourn et al., Immunotechnology, 2: 181 196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166 179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137 185 (Wiley-Liss, Inc. 1995).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., *Nature* 332(6162):323-7, 1988; Verhoeyen et al., *Science*. 239(4847):1534-6, 1988.). Such "humanized" antibodies are chimeric Abs (U.S. Pat. No. 4,816,567, 1989), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., *Nature* 332(6162):323-7, 1988; Verhoeyen et al., *Science*. 239(4847):1534-6, 1988.).

Human antibodies can also be produced using various techniques, including phage display libraries (Hoogenboom et al., *Mol Immunol*. (1991) 28(9):1027-37; Marks et al., *J Mol Biol*. (1991) 222(3):581-97) and the preparation of human monoclonal antibodies (Reisfeld and Sell, 1985, *Cancer Surv*. 4(1):271-90). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., High-avidity human IgG kappa monoclonal antibodies from a novel strain of minilocus transgenic mice, *Nat Biotechnol*. 1996 Jul.; 14(7):845-51; Lonberg et al., Antigen-specific human antibodies from mice comprising four distinct genetic modifications, *Nature* 1994 Apr. 28; 368 (6474):856-9; Lonberg and Huszar, Human antibodies from transgenic mice, *Int. Rev. Immunol*. 1995; 13(1):65-93; Marks et al., By-passing immunization: building high affinity human antibodies by chain shuffling. *Biotechnology* (N Y). 1992 Jul.; 10(7):779-83).

In some embodiments, a mono-specific anti-CCL2 antibody or fragment thereof suitable for the present invention has a binding affinity of or greater than approximately 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM. In some embodiments, a mono-specific anti-CCL2 antibody or fragment thereof suitable for the present invention has a binding affinity ranging between approximately 500 nM and 1 fM, between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM.

In some embodiments, a mono-specific anti-LOXL2 antibody or fragment thereof suitable for the present invention has a binding affinity of or greater than approximately 10 nM, 1 nM, 500 pM, 100 pM, 50 pM, 10 pM, 1 pM, 500 fM, 400 fM, 300 fM, 200 fM, 100 fM, 50 fM, 10 fM, 1 fM. In some embodiments, a mono-specific anti-LOXL2 antibody or fragment thereof suitable for the present invention has a binding affinity ranging between approximately 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM.

Bi-Specific Anti-CCL2 and Anti-LOXL2 Antibodies and Fusion Proteins

In some embodiments, the present invention provides bi-specific anti-CCL2 and anti-LOXL2 antibodies and/or fusion proteins. As used herein, the term "bi-specific antibodies or fusion proteins" encompasses any antibodies, fusion proteins, or fragments thereof, that contain at least two antigen-binding sites or antigen-binding arms with distinct specificities. For example, a bi-specific anti-CCL2 and anti-LOXL2 antibody or fusion protein suitable for the present invention contains at least a first antigen-binding site or arm that specifically binds to LOXL2 and at least a second antigen-binding site or arm that specifically binds to CCL2.

Each individual antigen-binding sites or arms of a bi-specific antibody may have desired binding affinity against its specific binding target (e.g., CCL2 or LOXL2). In some embodiments, an antigen-binding site or arm specifically binds to CCL2 with a binding affinity of or greater than approximately 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM. In some embodiments, an antigen-binding site or arm specifically binds to CCL2 with a binding affinity ranging between approximately 500 nM and 1 fM, between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM. In some embodiments, an antigen-binding site or arm specifically binds to LOXL2 with a binding affinity of or greater than approximately 10 nM, 1 nM, 500 pM, 100 pM, 50 pM, 10 pM, 1 pM, 500 fM, 400 fM, 300 fM, 200 fM, 100 fM, 50 fM, 10 fM, 1 fM. In some embodiments, an antigen-binding site or arm specifically binds to LOXL2 with a binding affinity ranging between approximately 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM. The present invention encompasses bi-specific antibodies with combinations of the anti-CCL2 and anti-LOXLs antigen binding sites or arms with any of the above described binding affinities. In particular, a bi-specific antibody may contain a first antigen-binding site or arm that specifically binds to LOXL2 with a binding affinity of 1 pM or greater and a second antigen-binding site or arm that binds to CCL2 with a binding affinity ranging between 500 nM and 1 fM. In particular, a bi-specific antibody may contain a first antigen-binding site or arm that specifically binds to LOXL2 with a binding affinity of 1 pM or greater and a second antigen-binding site or arm that binds to CCL2 with a binding affinity greater than 1 pM.

Each antigen-binding site of a bi-specific antibody can be independently a complete antigen-binding arm including a full length heavy chain and a full length light chain, an Fab fragment, a single-chain variable fragments (scFvs), or other forms of antibody fragments. In some embodiments, desired antigen-binding sites or arms may be prepared from mono-specific antibodies against CCL2 and LOXL2 produced using the techniques described above and then associating such desired anti-CCL2 and anti-LOXL2 antigen-binding sites or arms to produce desired bi-specific antibodies. For example, a desired anti-CCL2 or anti-LOXL2 antigen-binding site or arm may be isolated, separated or enzymatically digested from mono-specific monoclonal antibodies described above. Antigen-binding sites or arms of a bi-specific antibody can be arranged in various configurations that allow the two sites or arms to associate while retaining their antigen binding ability.

Suitable bi-specific antibodies or fusion proteins can be in various bi-specific antibody formats including, but not limited to, quadromas, chemical heteroconjugates, recombinant constructs using selected heterodimerization domains and recombinant constructs of minimal size consisting of two minimal antigen-binding sites. In general, quadromas look like monoclonal antibodies but have two different antigen-binding arms. Their classical way of production is based on the somatic fusion of two different hybridoma (fused between a tumor cell and an antibody-making normal cell) cells, each producing a unique monoclonal antibody (e.g., anti-CCL2 or anti-LOXL2 monoclonal antibody). Bi-specific antibodies with desired antigen-binding arms (e.g., anti-CCL2 and anti-LOXL2) can be produced by random pairing of two different antibody heavy and light chains. Various preferential pairing methods are available to reduce mispaired by-products and increase bi-specific antibody yield. For example, a murine and a rat hybridoma cell line can be fused that express monoclonal antibodies of particular IgG subclasses preferentially pairing with each other. Additionally, the preferential pairing of two different antibody heavy chains can be achieved by certain mutations in the CH3-domain of human IgG1, so-called "knobs-into-holes" strategy.

Quadroma format typically contains an Fc region, which can interact with Fc receptors. Therefore, bi-specific antibodies with an Fc part are also referred to as trispecific antibodies. In some embodiments, the Fc part of a quadroma can be enzymatic removed, resulting in bi-specific $F(ab')_2$ (the two antigen binding arms of an antibody chemically linked through (a) disulfide bond(s)). In addition, two antigen-binding sites or arms can be linked with thioether bonding or through one or more functional groups on the antibody or fragment including amine, carboxyl, phenyl, thiol, or hydroxyl groups.

In some embodiments, a bi-specific antibody can be produced by chemical coupling of two different monoclonal antibodies or antibody fragments with, e.g., a hetero-bifunctional crosslinker. For example, two different Fab's (monovalent antigen binding arm(s) of an antibody) can be chemically crosslinked at their hinge cysteine residues in a site-directed way. Examples of chemicals appropriate for chemical crosslinking or coupling include but are not limited to N-succinimidyl-3-(2-pyridyldithio)propionate) (SPDP), 1-Ethyl-3-(3-dimethylaminopropyl)carbodiimide hydrochloride (EDC), 5,5'-dithiobis-(2-nitrobenzoic acid) (DTNB), o-phenylene dimaleimide, carbodiimides, diisocyanates, diazobenzenes, hexamethylene diamines, dimaleimide, glutaraldehyde, 4-succinimidyl-oxycarbonyl-.alpha.-methyl .alpha.(2-pyridylthio)toluene (SMPT), N-succinimidyl-S acetyl-thioacetate (SATA), and combinations thereof.

In some embodiments, certain protein domains that naturally form heterodimers are used to construct heterodimeric bi-specific antibodies suited for large-scale expression. One example is the leucine zipper domains of transcription factors Fos and Jun which can be fused to the carboxy-terminus of two different Fab's or single-chain (sc) Fv (fragment of the variable region) antibody fragments. In some embodiments, antibody constant region domains Cκ and CH1 can be used instead of Fos and Jun dimerization domains for expression of the bi-specific antibody in bacteria such as *E. coli*. In certain embodiments, the two antigen-binding sites or arms can be associated via GST (glutathione S-transferase) fusion proteins, or a dimerization motifs thereof, PDZ dimerization domains, FK-506 BP (binding protein) or dimerization motifs thereof, natural or artificial helix-turn-helix dimerization domains (e.g., p53), Protein A or its dimerization domain, domain B, among others. In certain embodiments, two antigen-binding sites or arms may be associated via interaction with an exogenous component. For example, the two antigen-binding sites or arms may contain avidin motifs and both interact with added biotin.

In some embodiments, bi-specific antibodies include so called diabodies and tandem single-chain Fv constructs. Typically, these forms of bi-specific antibodies are made up from two different antigen-binding sites with minimal additional protein sequences acting as linker sequences. Each antigen binding site uses the minimal $V_H$ and $V_L$ domains from two antibody heavy and light chains, respectively. In diabodies, the $V_L$ domain of one antigen binding site is connected by a short peptide linker with the $V_H$ domain of the other antigen binding site and vice versa. Bi-specific antibodies in the tandem scFv format typically include two different $V_L/V_H$ pairs connected by a flexible peptide linker on a single protein chain. In some embodiments, tandem scFv constructs can be expressed in mammalian host cells which are capable of properly folding the four consecutively aligned antibody V regions. The fully functional bi-specific tandem single-chain antibodies are secreted into the cell culture supernatant and can be efficiently purified by affinity chromatography via a poly-histidine tag followed by size exclusion chromatography. Suitable peptide linkers may include any sequence that does not interfere with the conformation of the antigen binding sites or arms. In certain embodiments, a suitable peptide linker is 1, 2, 3, 4, 5, 6, 7, 8, 9, 10 or more amino acids long.

Antibodies produced by various methods described herein typically contain both homospecific and bi-specific molecules. Methods to assay for the presence of bi-specific monoclonals are known in the art, including bridge ELISA assays (see, e.g., Suresh et al. (1986) Proc. Natl. Acad. Sci. USA 83, 7989-93; Koolwijk et al. (1988) Hybridoma 7, 217-225; and De Lau et al. (1989) J. Immunol. 149, 1840-46). Double-antigen ELISA may be employed if sufficient quantities of the respective antigens are available.

The particular methods of bi-specific antibody preparation described above occasional result in the formation of monospecific as well as bi-specific antibodies (e.g., following procedures of chemical coupling). When this occurs, the desired bi-specific antibodies can be separated from the monospecific ones by any of a variety of procedures which allow differentiation between the two forms. Such procedures include but are not limited to passive elution from preparative, non-denaturing acrylamide gels or various conventional chromatographic techniques, e.g., anion-exchange, HPLC, or thiophilic adsorption chromatography (see, e.g., Kreutz et al. (1998). J. Chromatography 14, 161-170). Additionally, each of the antigen-binding sites or arms may be tagged with a different tag, and doubly tagged, bi-specific antibodies are separated from singly tagged monospecific antibodies by dual affinity chromatography.

Additional methods of generating, purifying and characterizing bi-specific antibodies are known in the art; for example, as disclosed in U.S. Pat. Nos. 5,601,819; 6,004,555, 5,762,930; 6,060,285; 6,010,902; 5,959,083; 5,807,706, and U.S. Patent Publication No. 2002/0025317, each of which is incorporated by reference herein.

Desired bi-specific anti-CCL2 and anti-LOXL2 antibodies can be further modified to produce chimeric, humanized, or fully human bi-specific antibodies using standard methods known in the art including various methods described herein.

Treatment of Scleroderma and Related Diseases, Disorders or Conditions

Bi-specific and/or mono-specific anti-CCL2 and anti-LOXL2 molecules (e.g., antibodies, fynomers, aptamers, fusion proteins, or protein binding domains) described herein may be used to effectively treat individuals suffering from or susceptible to scleroderma or related fibrotic, inflammatory diseases, disorders or conditions. The terms, "treat" or "treatment," as used herein, refers to amelioration of one or more symptoms, prevention or delay of the onset of one or more symptoms, and/or lessening of the severity or frequency of one or more symptoms of the relevant disease, disorder or condition.

Various molecules of the invention may be administered alone or in combination. In some embodiments, a method of treatment according to the present invention involves administering a bi-specific molecule described herein into a subject in need of treatment. In some embodiments, a method of treatment according to the present invention involves administering an anti-CCL2 and an anti-LOXL2 mono-specific antibodies, or fragments thereof, described herein into a subject in need of treatment. Anti-CCL2 and anti-LOXL2 mono-specific antibodies, or fragments thereof, can be administered simultaneously or sequentially, via same or different administration routes.

In some embodiments, molecules described herein may be administered alone or in conjunction with other therapeutic agents, such as those that are useful in treating fibrotic or inflammatory diseases, disorders or conditions. Such therapeutic agents include, but are not limited to, corticosteroids, NSAIDs, immune-suppressing drugs (e.g., Metotrexate and Cytoxan), small molecule immunomodulators, interferon receptor antibodies, anti-fibrotic drugs including D-penicillamine, colchicine, PUVA, relaxin, and cyclosporine and anti-TGFbeta treatments, and endothelin receptor antagonists.

In some embodiments, molecules described herein can be administered using conventional doses and delivery methods, such as those described for other, comparable therapeutic agents. Dosages to be administered can be determined by conventional procedures known to those of skill in the art. See, e.g., The Pharmacological Basis of Therapeutics, Goodman and Gilman, eds., Macmillan Publishing Co., New York. In general, effective dosages are those which are large enough to produce the desired effect, e.g., neutralizing CCL2 and/or LOXL2 and/or blocking the binding of CCL2 and/or LOXL2 to their cognate receptors. The dosage should not be so large as to cause adverse side effects, such as unwanted cross-reactions, anaphylactic reactions, and the like. Factors to be considered include the activity of the specific antibody/agent involved, its metabolic stability and length of action, mode and time of administration, drug combination, rate of excretion, and the age, body weight, general health, sex, diet, and severity of the particular disease-states of the host undergoing therapy.

Molecules described herein can be administered in any dosing regimen that is therapeutically effective. In some embodiments, anti-CCL2/LOXL2 bi-specific or mono-specific antibodies are administered at bimonthly, monthly, triweekly, biweekly, weekly, daily, or at variable intervals.

Molecules described herein can be administered using any method of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. When a combination of anti-CCL2 and anti-LOXL2 antibodies are used, anti-CCL2 and anti-LOXL2 antibodies can be administered via the same administration route or via different administration routes.

Scleroderma

In some embodiments, methods and compositions described herein can be used to treat a subject who is suffering or susceptible to all forms of scleroderma, including, the limited systemic sclerosis/scleroderma, the diffuse systemic sclerosis/scleroderma, and other forms of scleroderma. Limited systemic sclerosis/scleroderma typically involves cutaneous manifestations that mainly affect the hands, arms and face. It is also known as CREST syndrome in reference to the following complications: Calcinosis, Raynaud's phenomenon, Esophageal dysfunction, Sclerodactyly, and Telangiectasias. Additionally, pulmonary arterial hypertension may occur in up to one-third of patients, and is the most serious complication for this form of scleroderma. Diffuse systemic sclerosis/scleroderma is rapidly progressing and affects a large area of the skin and one or more internal organs, frequently the kidneys, esophagus, heart and lungs. Other forms of scleroderma include systemic sine scleroderma, which lacks skin changes, but has systemic manifestations, and two localized forms which affect the skin, but not the internal organs: morphea and linear scleroderma.

In some embodiments, treatment refers to partially or completely alleviation, amelioration, relief, inhibition, delaying onset, reducing severity and/or incidence of one or more symptoms associated with scleroderma, including but not limited to, endothelial-cell damage, proliferation of basal-lamina layers, perivascular mononuclear-cell infiltration, fibrosis, derangement of visceral-organ architecture, rarefaction of blood vessels, hypoxia, swelling of the fingers, dorsa, and forearms, sensations of coldness in the extremities, digital ulcers, elongation of nail folds, pitted bleeding of the nails, pitting scars on the nails, pulmonary hypertension, skin fibrosis, hair loss, skin tightness, skin hardness, hyperpigmentation, hypopigmentation, itching of the skin, carpal tunnel syndrome, muscle weakness, joint pain, joint stiffness, kidney fibrosis, esophageal fibrosis, mouth fibrosis, heart fibrosis, and lung fibrosis, liver fibrosis, muscle fibrosis, dry cough, shortness of breath, difficulty breathing, alveolitis, pneumonia, wheezing, bloating after meals, constipation, diarrhea, difficulty swallowing, gastric antral vascular ectasia, esophageal reflux, heartburn, fecal incontinence, flat white patches in the mouth, loss of attached gingival mucosa, gingival recession, diffuse widening of the periodontal ligament, dysphagia, inelasticity of the mouth, resorption of posterior ramus of the mandible, coronoid process, and condyle, cancer, heart failure, pulmonary hypertension, kidney failure, malabsorption, or any combination thereof, as compared to an untreated control or the pre-treatment state.

In some embodiments, treatment refers to partially or completely alleviation, amelioration, relief, inhibition, delaying onset, reducing severity and/or incidence of fibrosis. As used herein, the term "fibrosis" refers to the formation of an excess fibrous connective tissue in an organ or tissue. Without wishing to be bound by particular theory, it is thought that fibrosis may be caused by activation of certain fibroblast. Different subtypes of fibroblasts are known to perform diverse functions, even within a single tissue. For example, papillary fibroblasts of the upper layers of the skin produce thin collagen bundles and have a high rate of proliferation, whereas reticular fibroblasts from the deeper dermal layer of the skin produce thick collagen bundles and abundant versican, and promote rapid lattice contraction. Fibroblasts can be in a quiescent state or at varying stages of activation. During normal cellular function, fibroblasts become activated, for example, in response to injury to facilitate wound healing. Activated fibroblasts produce increased components of the extracellular matrix, including collagen and collagen modifying enzymes. In individuals with scleroderma, an increase in fibroblast activation is generally observed, accompanied by an overproduction of the ECM. This overproduction of the ECM is generally believed to cause fibrosis, the formation of excess fibrous connective tissue in an organ or tissue, that is a characteristic of scleroderma.

In some embodiments, treatment refers to partially or completely alleviation, amelioration, relief, inhibition, delaying onset, reducing severity and/or incidence of fibrosis in skin, kidney, liver, lung and/or oesophagus.

Figure 2:
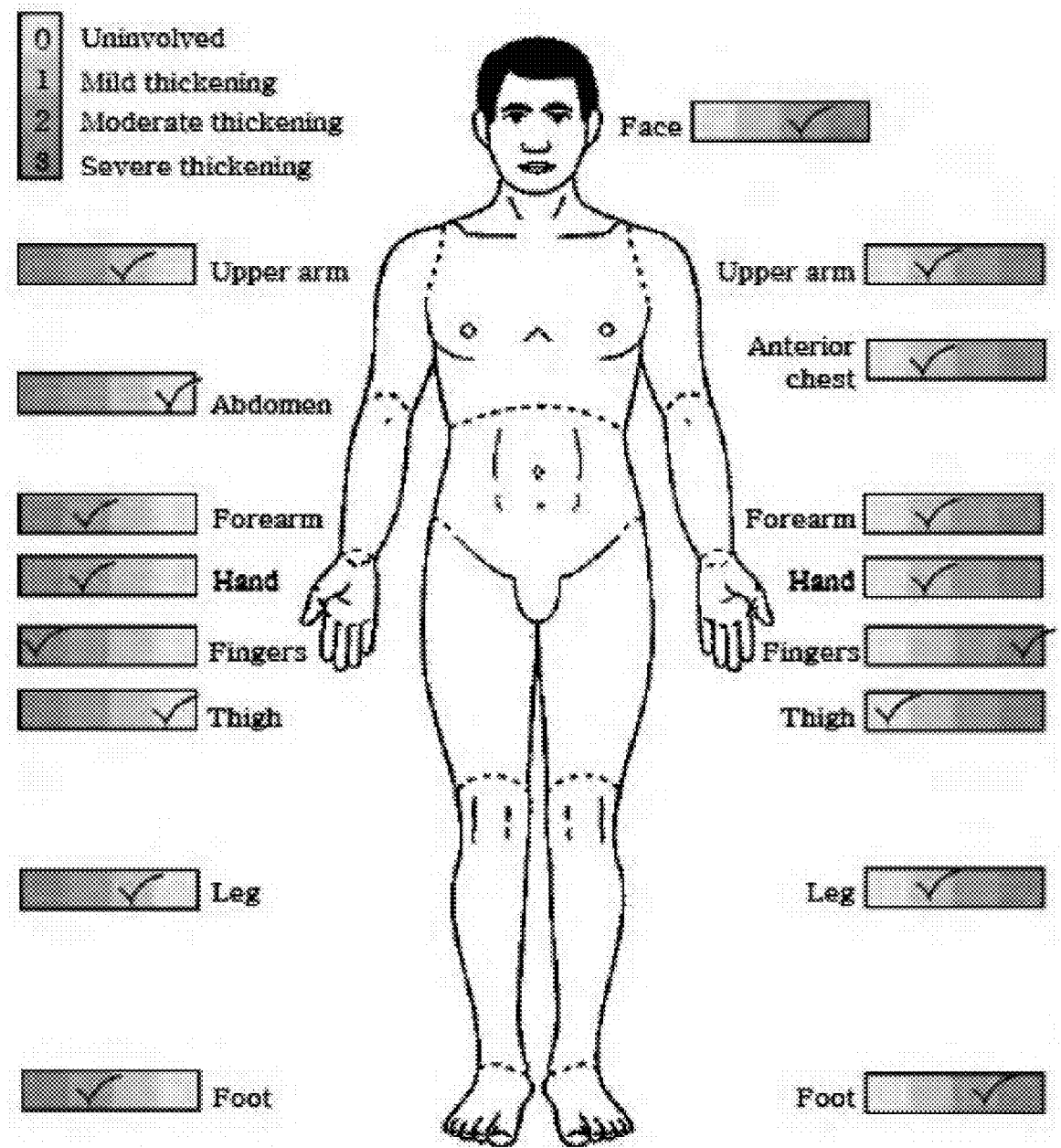
FIG. 2 illustrates an exemplary diagram depicting the Modified Rodnan Skin Score. Locations on the body where skin fibrosis is assessed are indicated.

In some embodiments, treatment results in partially or completely alleviation, amelioration, relief, inhibition, delaying onset, reducing severity and/or incidence of skin fibrosis. Typically, skin fibrosis is associated with skin thickening, hardening, or formation of scars (e.g., keloid or burn scar, etc.). In some embodiments, skin fibrosis is assessed by Modified Rodnan Skin Score. For example, as illustrated in FIG. 2 uninvolved skin is given a score 0; mild thickening is given a score 1; moderate thickening is given a score 2; and severe thickening is given a score 3. In some embodiments, treatment results in a reduction of Modified Rodnan Skin Score by more than 10%, more than 15%, more than 20%, more than 25%, more than 30%, more than 35%, more than 40%, more than 45%, more then 50%, more than 55%, more than 60%, more than 65%, more than 70%, more than 75%, more than 80%, more than 85%, more than 90%, more than 95%, or more, as compared to the pre-treatment state. In some embodiments, treatment results in substantial elimination of skin fibrosis.

Without wishing to be bound by theory, it is also thought that activation of fibroblasts in scleroderma patients may be caused by the activation of the immune response by the production of cytokines. Examples of cytokines include but are not limited to TGF-β, CCL2, CTGF, ET-1, Fibroblast Growth Factor, IL-1, IL-4, IL-6, IL-12, IL-13, IL-17, MCP-1, MCP-3, and PDGF. Cytokines can be produced by pro-inflammatory cells of the immune system, for example activated T-cells, monocytes, or macrophages or, alternatively, cytokines can be produced by epithelial cells. One factor contributing to the activation of fibroblasts may be perivascular infiltrates of mononuclear cells in the dermis associated with increased capillary permeability. Alternative or additional means of fibroblast activation include interaction with the extracellular matrix and/or mechanical tension. Thus, in some embodiments, treatment of scleroderma patients according to the present invention results in reduction of the production of one or more pro-inflammatory cytokines, such as those described herein. In some embodiments, treatment results in a reduction of a pro-inflammatory cytokine (e.g., TGF-β, CCL2, CTGF, ET-1, Fibroblast Growth Factor, IL-1, IL-4, IL-6, IL-12, IL-13, IL-17, MCP-1, MCP-3, and/or PDGF) by more than 10%, more than 15%, more than 20%, more than 25%, more than 30%, more than 35%, more than 40%, more than 45%, more then 50%, more than 55%, more than 60%, more than 65%, more than 70%, more than 75%, more than 80%, more than 85%, more than 90%, more than 95%, or more, as compared to the pre-treatment state. Various methods for determining the level of cytokines are known in the art and can be used to practice the present invention.

In some embodiments, treatment results in reduced CCL2 serum levels. In some embodiments, treatment results in a reduction of CCL2 serum levels by more than 10%, more than 15%, more than 20%, more than 25%, more than 30%, more than 35%, more than 40%, more than 45%, more then 50%, more than 55%, more than 60%, more than 65%, more than 70%, more than 75%, more than 80%, more than 85%, more than 90%, more than 95%, or more, as compared to the pre-treatment state. In some embodiments, treatment results in a CCL2 serum level of less than about 800 pg/ml, 700 pg/ml, 600 pg/ml, 500 pg/ml, 400 pg/ml, 350 pg/ml, 300 pg/ml, 250 pg/ml, 200 pg/ml, 150 pg/ml, or 100 pg/ml. In some embodiments, treatment results in a CCL2 serum level comparable to that of a healthy control of substantially same age or developmental stage.

Fibrotic Diseases, Disorders or Conditions

In addition to Scleroderma, methods and compositions according to the present invention can be used to treat fibrotic diseases, disorders or conditions in general including, but not limited to, multifocal fibrosclerosis, sclerodermatous graft-vs-host-disease, nephrogenic systemic fibrosis, organ specific fibrosis, and the like. Illustrative organ specific fibrotic disorders include, but are not limited to, pulmonary fibrosis, pulmonary hypertension, cystic fibrosis, asthma, chronic obstructive pulmonary disease, liver fibrosis, kidney fibrosis, NASH, and the like. Many fibrotic diseases, disorders or conditions have disordered and/or exaggerated deposition of extracellular matrix in affected tissues. Fibrosis may be associated with inflammation, occur as a symptom of underlying disease, and/or caused by surgical procedure or wound healing process. Unchecked fibrosis can result in destruction of the architecture of the underlying organ or tissue, commonly referred to as scarring.

NASH is usually a silent disease with few or no symptoms. Patients generally feel well in the early stages and only begin to have symptoms—such as fatigue, weight loss, and weakness—once the disease is more advanced or cirrhosis develops. The progression of NASH can take years, even decades. The process can stop and, in some cases may even begin to reverse on its own without specific therapy. Or NASH can slowly worsen, causing scarring or fibrosis to appear and accumulate in the liver. As fibrosis worsens, cirrhosis develops in which the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

Kidney (renal) fibrosis results from excessive formation of fibrous connective tissue in the kidney. Kidney fibrosis causes significant morbidity and mortality and leads to a need for dialysis or kidney transplantation. Fibrosis can occur in either the filtering or reabsorptive component of the nephron, the functional unit of the kidney. A number of factors may contribute to kidney scarring, particularly derangements of physiology involved in the autoregulation of glomerular filtration. This in turn leads to replacement of normal structures with accumulated extracellular matrix. A spectrum of changes in the physiology of individual cells leads to the production of numerous peptide and non-peptide fibrogens that stimulate alterations in the balance between extracellular matrix synthesis and degradation to favor scarring.

Inflammatory Diseases, Disorders or Conditions

In some embodiments, methods and compositions according to the present invention are used to treat inflammatory diseases, disorders or conditions including, but not limited to: Systemic Inflammatory Response (SIRS); Alzheimer's Disease (and associated conditions and symptoms including: chronic neuroinflammation, glial activation; increased microglia; neuritic plaque formation; and response to therapy); Amyotropic Lateral Sclerosis (ALS), arthritis (and associated conditions and symptoms including, but not limited to: acute joint inflammation, antigen-induced arthritis, arthritis associated with chronic lymphocytic thyroiditis, collagen-induced arthritis, juvenile arthritis; rheumatoid arthritis, osteoarthritis, prognosis and *streptococcus*-induced arthritis, spondyloarthopathies, gouty arthritis), asthma (and associated conditions and symptoms, including: bronchial asthma; chronic obstructive airway disease; chronic obstructive pulmonary disease, juvenile asthma and occupational asthma); cardiovascular diseases (and associated conditions and symptoms, including atherosclerosis; autoimmune myocarditis, chronic cardiac hypoxia, congestive heart failure, coronary artery disease, cardiomyopathy and cardiac cell dysfunction, including: aortic smooth muscle cell activation; cardiac cell apoptosis; and immunomodulation of cardiac cell function; diabetes and associated conditions and symptoms, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations such as viral and other types of hepatitis, cholesterol gallstones and hepatic fibrosis, HIV infection (and associated conditions and symptoms, including degenerative responses, neurodegenerative responses, and HIV associated Hodgkin's Disease), Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis; multiple sclerosis, nephropathies (and associated diseases and conditions, including diabetic nephropathy, endstage renal disease, acute and chronic glomerulonephritis, acute and chronic interstitial nephritis, lupus nephritis, Goodpasture's syndrome, hemodialysis survival and renal ischemic reperfusion injury), neurodegenerative diseases (and associated diseases and conditions, including acute neurodegeneration, induction of IL-1 in aging and neurodegenerative disease, IL-1 induced plasticity of hypothalamic neurons and chronic stress hyperresponsiveness), opthalmopathies (and associated diseases and conditions, including diabetic retinopathy, Graves' opthalmopathy, and uveitis, osteoporosis (and associated diseases and conditions, including alveolar, femoral, radial, vertebral or wrist bone loss or fracture incidence, postmenopausal bone loss, mass, fracture incidence or rate of bone loss), otitis media (adult or pediatric), pancreatitis or pancreatic acinitis, periodontal disease (and associated diseases and conditions, including adult, early onset and diabetic); pulmonary diseases, including chronic lung disease, chronic sinusitis, hyaline membrane disease, hypoxia and pulmonary disease in SIDS; restenosis of coronary or other vascular grafts; rheumatism including rheumatoid arthritis, rheumatic Aschoff bodies, rheumatic diseases and rheumatic myocarditis; thyroiditis including chronic lymphocytic thyroiditis; urinary tract infections including chronic prostatitis, chronic pelvic pain syndrome and urolithiasis Immunological disorders, including autoimmune diseases, such as alopecia aerata, autoimmune myocarditis, Graves' disease, Graves opthalmopathy, lichen sclerosis, multiple sclerosis, psoriasis, systemic lupus erythematosus, systemic sclerosis, thyroid diseases (e.g. goiter and struma lymphomatosa (Hashimoto's thyroiditis, lymphadenoid goiter), sleep disorders and chronic fatigue syndrome and obesity (non-diabetic or associated with diabetes). Resistance to infectious diseases, such as Leishmaniasis, Leprosy, Lyme Disease, Lyme Carditis, malaria, cerebral malaria, meningitis, tubulointerstitial nephritis associated with malaria), which are caused by bacteria, viruses (e.g. cytomegalovirus, encephalitis, Epstein-Barr Virus, Human Immunodeficiency Virus, Influenza Virus) or protozoans (e.g., *Plasmodium falciparum*, trypanosomes). Response to trauma, including cerebral trauma (including strokes and ischemias, encephalitis, encephalopathies, epilepsy, perinatal brain injury, prolonged febrile seizures, SIDS and subarachnoid hemorrhage), low birth weight (e.g. cerebral palsy), lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries). Hormonal regulation including fertility/fecundity, likelihood of a pregnancy, incidence of preterm labor, prenatal and neonatal complications including preterm low birth weight, cerebral palsy, septicemia, hypothyroidism, oxygen dependence, cranial abnormality, early onset menopause. A subject's response to transplant (rejection or acceptance), acute phase response (e.g. febrile response), general inflammatory response, acute respiratory distress response, acute systemic inflammatory response, wound healing, adhesion, immunoinflammatory response, neuroendocrine response, fever development and resistance, acute-phase response, stress response, disease susceptibility, repetitive motion stress, tennis elbow, and pain management and response.

Biomarkers or Indicators for Patient Stratification, Treatment Monitoring and/or Optimization In some embodiments, methods and compositions based on anti-CCL2/LOXL2 bi-specific or mono-specific molecules (e.g., antibodies, fynomers, aptamers, fusion proteins, or protein binding domains) described herein can be used with biomarkers for patient stratification, treatment monitoring and/or optimization. In some embodiments, suitable biomarkers are differentially expressed biomarkers. As used herein, the term "differentially expressed biomarker" refers to a biomarker whose level of expression is different in a subject (or a population of subjects) afflicted with scleroderma relative to its level of expression in a healthy or normal subject (or a population of healthy or normal subjects). The term also encompasses a biomarker whose level of expression is different for a different disease subtype (i.e., Limited cutaneous or diffuse cutaneous). The term further encompasses a biomarker whose level of expression is different at different stages of the disease (e.g., mild or early scleroderma, severe or late scleroderma). Differential expression includes quantitative, as well as qualitative, differences in the temporal or cellular expression pattern of the biomarker. As described in greater details below, a differentially expressed biomarker, alone or in combination with other differentially expressed biomarkers, is useful in a variety of different applications in diagnostic, staging, therapeutic, drug development and related areas. The expression patterns of the differentially expressed biomarkers disclosed herein can be described as a fingerprint or a signature of scleroderma, scleroderma subtype, scleroderma stage and scleroderma disease severity and/or progression. They can be used as a point of reference to compare and characterize unknown samples and samples for which further information is sought. The term "decreased level of expression", as used herein, refers to a decrease in expression of at least 10% or more, for example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more as measured by one or more methods described herein. The term "increased level of expression", as used herein, refers to an increase in expression of at least 10% or more, for example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more as measured by one or more methods, such as method described herein.

Skin Gene Expression Analysis

Various methods for identifying differentially expressed biomarkers in scleroderma patients are known in the art and can be used to practice the present invention. For example, skin gene expression analysis can be a powerful tool for subsetting patients, identifying protein biomarkers and indicators of responsive patient subsets. In some embodiments, genes that are differentially regulated in patients with scleroderma can be identified by comparing transcriptional profiles of skin samples of healthy individuals with those having scleroderma. Further, gene transcripts that associate with severity of disease can be identified by including scleroderma patients at various stages of degree progression. Transcriptional profiles can be analyzed by microarray analysis, as has been described, for example, by Milano et al. in "Molecular Subsets in the Gene Expression Signatures of Scleroderma Skin" (PLOS One, 3:7, 1-18, 2008), the entirety of which is herein incorporated by reference. For example, microarray analysis can be performed on skin samples (e.g., forearm and back samples) from patients with diffuse scleroderma, limited scleroderma, morphea (a disease similar to scleroderma with no internal organ involvement) and healthy controls. To identify genes most highly associated with scleroderma, the genes that are most internally consistent between replicates and sample sites, while being the most variable between individuals, are selected for further analysis. Cluster analysis based on differential gene expression correlated with severity of scleroderma can be used to select genes affected by scleroderma.

It has been reported that differentially expressed exemplary genes in scleroderma can be clustered into 6 groups. The first group includes immunoglobulin genes expressed highly in a subset of patients with diffuse scleroderma and in patients with morphea, including but not limited to CCR2, CCL4, and IGLL1. The second group includes proliferation signature, including genes that are expressed only when the cell is dividing. Genes showing increased expression in this cluster include the cell-cycle regulated genes such as CKS1B, CDKS2, CDCl$_2$, MCM8 and E2F7. The existence of a proliferation signature is consistent with reports from skin biopsies demonstrating that cells of diffuse scleroderma tissue undergoing increased proliferation. The third group includes collagen and extracelluar matrix components, including but not limited to COL5A2, COL8A1, COL10A1, COL12A1. The fourth group includes genes typically associated with the presence of T-lymphocyes and macrophages, which are similarly expressed to the third group and include PTPRC, which is required for T-cell activation, as well as CD2 and CDW52, that are expressed on the surface of T lymphocytes. The fifth group includes genes showing low expression in diffuse scleroderma. These genes show higher expression levels in other biopsies and include WIF1, Tetranectin, IGFBP6, and IGFBP5, among others. The final group is a heterogeneous gene expression cluster that is high in limited scleroderma and a subset of diffuse scleroderma, including but not limited to, UTS2R, GALR3, PARD6G, PSEN1, PHOX2A, CENTG3, HCN4, KLF16, and GPR15G. Additional differentially expressed exemplary genes are described in Milano et al. in "Molecular Subsets in the Gene Expression Signatures of Scleroderma Skin" (PLOS One, 3:7, 1-18, 2008), the entirety of which is herein incorporated by reference.

Multi-Gene Signature as Surrogate Markers

Combinations of genes may be used as biomarkers. Exemplary methods for biomarker identification is provided in, for example, Farina et al., in "A Four-Gene Biomarker Predicts Skin Disease in Patients with Diffuse Cutaneous Systemic Sclerosis" (Arthritis Rheum. 62(2), 580-588, 2010), the entirety of which is incorporated herein by reference. Starting with targets such as TGFB and interferon known to be regulated in scleroderma, Farina identified a four-gene biomarker, including the genes CTGF, THS1, COL4, and PAI1. The transcription of these four genes in combination was found to be highly correlated with Modified Rodnan Skin Score (mRSS) and highly predictive of diffuse scleroderma.

mRSS is used as one clinical marker of scleroderma. Typically, mRRS is assigned as shown in FIG. 2: uninvolved skin is assigned a score 0; mild thickening is given a score 1; moderate thickening is given a score 2; and severe thickening is given a score 3. Typically, a total mRSS score ranging from 0-51 can be determined based on a grading of 0-3 at 17 skin areas of a patient. mRSS can be used as indicators for diagnosis and monitoring treatment alone or in combination with other biomarkers..

Similar strategy can be used to identify and validate potential signature biomarkers for scleroderma. Specifically, gene transcripts identified as positively or negatively regulated in scleroderma are tested alone or in combination to identify biomarkers comprised of gene transcript(s) or combinations of gene transcripts that are most highly correlated with clinical markers of scleroderma. In addition to mRSS, other clinical markers can be used, such as the HAQ-DI, DLCO, or FVC.

CCL2 Levels

CCL2 levels, for example, CCL2 serum levels, can be used as biomarker or indicators for determining disease severity, organ involvement, selecting appropriate treatment, monitoring disease progression and patient response. To determine CCL2 levels as biomarkers or indicators, CCL2 levels in the serum of patients at a variety of stages of scleroderma and unaffected individuals are determined. This can be done by assaying CCL2 protein levels in serum by, e.g., ELISA, and correlated with skin and other organ (e.g., lung, liver, kidney, oesophagus) involvement. Exemplary methods are described in Carulli et al. Ann Rheum Dis. 67:105-109, 2008.

CCL2 levels present in skin, such as from a biopsy, and/or serum can also be correlated with mRSS or other clinical markers, such as the Health Assessment Questionnaire (HAQ-DI), Diffusing capacity of the lung for carbon monoxide (DLCO), or Forced Vital Capacity (FVC).

Various biomarkers can be used alone or in combination, or alternatively, together with clinical diagnostic markers, such as mRSS, to stratify patients based on severity of scleroderma, selecting proper therapy or dosing regimen, evaluating the effectiveness of a therapy, monitoring responsiveness to therapy, prognosis for disease course, and measurement of disease progression in a subject. Typically, in such methods, levels of suitable biomarkers (e.g., such as those selected from various differentially expressed genes described herein and other known markers such as CCL2 levels) determined for a biological sample obtained from the subject from one or more time points are compared to the levels from the subject from one or more other time points. For example, biomarker levels may be measured before or at the beginning of a treatment course. Biomarker levels may be measured at one or more time points throughout the course of treatment and compared with the level before the treatment or from an earlier time point of a treatment course. Identification or selection of appropriate treatment, determining if a patient has positive response to a treatment and/or optimization of the treatment can be determined based on the evaluation of biomarkers.

Pharmaceutical Compositions

The present invention also provides compositions comprising one or more provided molecules (e.g., antibodies, fynomers, aptamers, fusion proteins, protein binding domains). In some embodiments the present invention provides at least one molecule and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of scleroderma or of negative ramifications associated or correlated with scleroderma. In some embodiments, provided pharmaceutical compositions are useful in therapeutic applications, for example in individuals suffering from or susceptible to scleroderma. In some embodiments, pharmaceutical compositions are formulated for administration to humans.

For example, pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in molecular degradation.

Liquid dosage forms and/or reconstituted solutions may comprise particulate matter and/or discoloration prior to administration. In some embodiments, a solution should not be used if discolored or cloudy and/or if particulate matter remains after filtration.

Compositions of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

EXAMPLES

The present invention will be further illustrated by the following non-limiting examples. These Examples are set forth to aid in the understanding of the invention but are not intended to, and should not be construed to, limit its scope in any way. The Examples do not include detailed descriptions of conventional methods that would be well known to those of ordinary skill in the art. Unless indicated otherwise, parts are parts by weight, molecular weight is average molecular weight, temperature is indicated in Celsius, and pressure is at or near atmospheric.

Example 1. Preparation of Bi-specific Anti-CCL2/LOXL2 Antibodies

This example illustrates preparation of bi-specific anti-CCL2/LOXL2 antibodies. As described above, various methods are available to generate and select bi-specific antibodies with desired specificities and binding affinities.

In this particular example, the bi-specific antibody is composed of a complete antigen-binding arm against CCL2 and a complete antigen-binding arm against LOLX2. Specifically, a mouse cell line producing a humanized CCL2-specific monoclonal antibody is fused to a rat cell line producing a humanized LOXL2-specific monoclonal antibody to produce a quadroma. Supernatants of quadroma cells are tested for binding to target cells by FACS analysis. Antibodies are purified from quadroma cell culture by protein A affinity followed by ion exchange chromatography.

Example 2. Dose Range Testing

This example illustrates a dose response study designed to evaluate effective dose ranges of bi-specific anti-CCL2 and anti-LOXL2 antibody for treatment of scleroderma.

A bleomycin induced scleroderma mouse model is used in this example. Typically, fibrosis is induced in mice by repeated subcutaneous injection of bleomycin, polyinosinic-polycytidylic acid and/or LPS into the dorsal skin. Specifically, osmotic pumps (7-day) containing either bleomycin at concentration of 10-110 μg and up to 200 μg, LPS at a concentration of 300 μg, polycytidylic acid at a concentration of 100 μg or PBS alone are implanted subcutaneously into groups of 10 B6 mice. In this mouse model, histopathological changes in the skin closely resembles that seen in scleroderma. Early mononuclear cell accumulation and upregulated TGF-0 and chemokine expression is followed by dermal fibrosis characterized by thick collagen bundles and accumulation of activated fibroblasts. Mice also manifest evidence of pulmonary and renal fibrosis.

Dose(s) of bi-specific CCL2/LOXL2 antibody or a control antibody escalating concentrations are administered into the mice via intraperitoneal injection.

Example 3. In Vivo Efficacy of Bi-Specific Anti-CCL2/LOXL2 Antibody

This example illustrates a study designed to evaluate the effect of treatment with anti-CCL2/LOXL2 antibodies on inflammation and fibrosis in the bleomycin mouse model for scleroderma.

7 or 28-day osmotic pumps containing either PBS alone or 10-110 μg and up to 200 μg bleomycin in PBS will be implanted subcutaneously into B6 mice. Every two days, mice will be treated via intraperitoneal injection with anti-CCL2/LOXL2 bi-specific antibody at suitable concentrations, as determined in example 2, or with a control antibody.

After 7 days, in the case of a 7 day osmotic pump, or 28 days, in the case of a 28 day osmotic pump, skin and lung tissue will be harvested for transcriptional and histological analysis. Levels of CCL2 protein in tissue samples is measured by ELISA. For transcriptional analysis, RNA is extracted from skin tissue and the isolated RNA is subject to and semi-quantitative or quantitative reverse transcriptase-PCR using techniques commonly known in the art. Levels of TGFβ gene expression and gene expression levels of pro-inflammatory genes, including but not limited to PAI1, COMP, COL1a1, F4/80, IL-6, and TNFα is measured using commercially available primers (TaqMan®). For histological analysis, skin fibrosis is analyzed by microscopic examination of tissue sections stained with hematoxylin and eosin (H&E). The use of H&E staining to visualize tissue morphology is well known in the art Immunohistochemistry is used to quantify monocyte infiltration by microscopic examination of tissue sections probed with the monocyte specific anti-F4/80 antibody using techniques well known in the art.

It is anticipated that treatment with anti-CCL2/LOXL2 antibody will reduce infiltration of monocytes and macrophages, will reduce inflammatory gene expression (ex., IL-6, TNFα), and will decrease TGFβ-induced marker gene expression. This is expected to result in a general decrease in fibrosis.

Example 4. Therapeutic Modeling

This example illustrates a model of CCL2 production and turnover in various tissues and plasma to predict tissue target levels. The illustrated model represents an extreme presentation of high CCL2 levels.

Typically, CCL2 is produced in disease tissues and secreted into plasma. In healthy individuals, CCL2 synthesis in skin is low or undetectable. CCL2 synthesis increases with involvement of total skin in both non-affected and affected skin, leading to increased serum CCL2 levels. Serum CCL2 levels further increase with organ involvement. Typically, healthy individuals have an average serum CCL2 level of less than about 100 pg/ml. Individuals having so called Raynaud's phenomenon has slightly increased average serum CCL2 levels. Patients suffering from sclerosis typically have an average serum CCL2 level of about 250 pg/ml. Patients suffering from limited cutaneous systemic sclerosis typically have an average serum CCL2 level of about 250 pg/ml. Patients suffering from diffuse cutaneous systemic sclerosis typically have an average serum CCL2 level of about 380 pg/ml. Patients suffering from limited cutaneous systemic sclerosis typically have an average serum CCL2 level of about 250 pg/ml.

Figure 3:
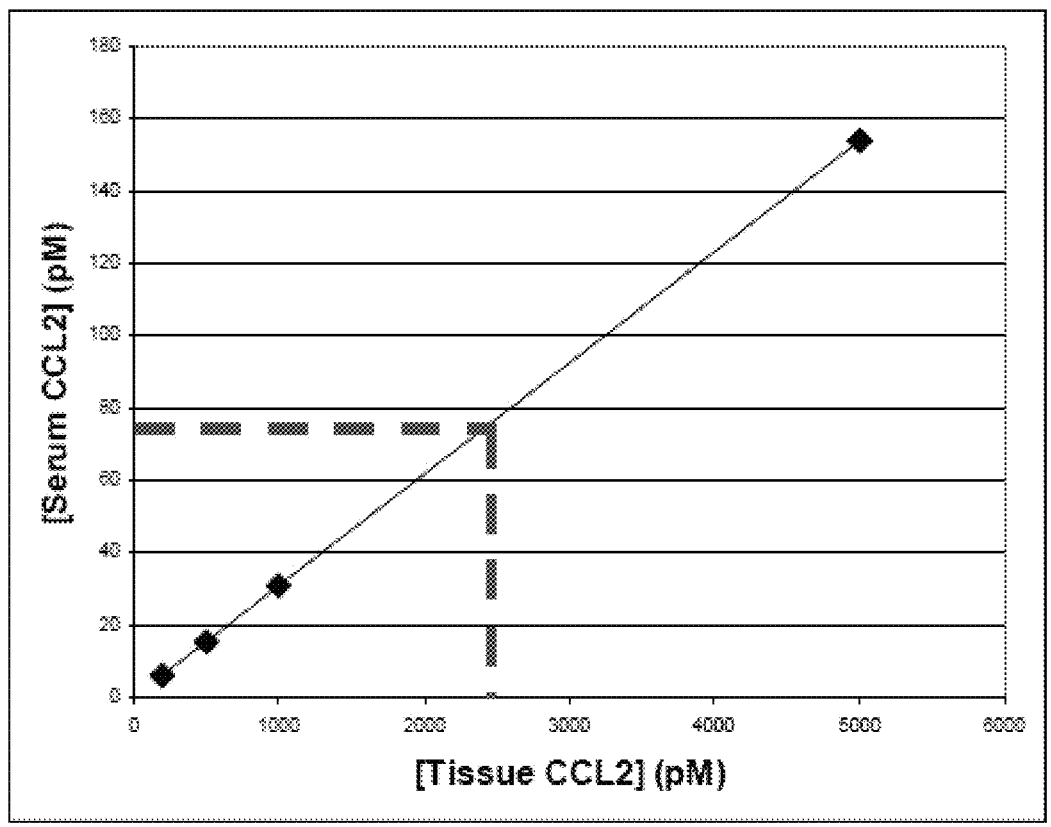
FIG. 3 depicts an exemplary graph plotting serum and tissue concentration of CCL2 following equilibration.

The molecular weight of CCL2 is about 8.6 kDa, which is much smaller than the glomerular filtration threshold of about 50 kDa, resulting in rapid kidney clearance. CCL2 is internalized by active receptor mediated internalization. Typical kd for CCL2 to bind its receptor CCR2 is about 60 pM-2 nM. CCR2 is primarily present on lymphoid-origin cells and lymphatic endothelium. It is contemplated that scleroderma causes increased vascular permeability early in disease progression, which permits substantial equilibration of CCL2 and any therapeutic antibodies between interstitium and serum. Therefore, serum half-life of CCL2 is about 10 minutes based on data from mice and rabbits. It is expected that CCL2 serum half-life in humans is similar. Relatively permeable tissue allows CCL2 reach equilibration from tissue to serum (half-max) quickly, for example in about 2 hours. In some cases, serum CCL2 level may reach 1000 pg/ml (~75 pM) with whole skin involvement but without organ involvement. A target profile showing serum and tissue CCL2 equilibration is shown in FIG. 3, which predicts the desired amount of antibodies need to neutralize 3 nM of tissue CCL2 and compete it off its receptor.

Figure 4:
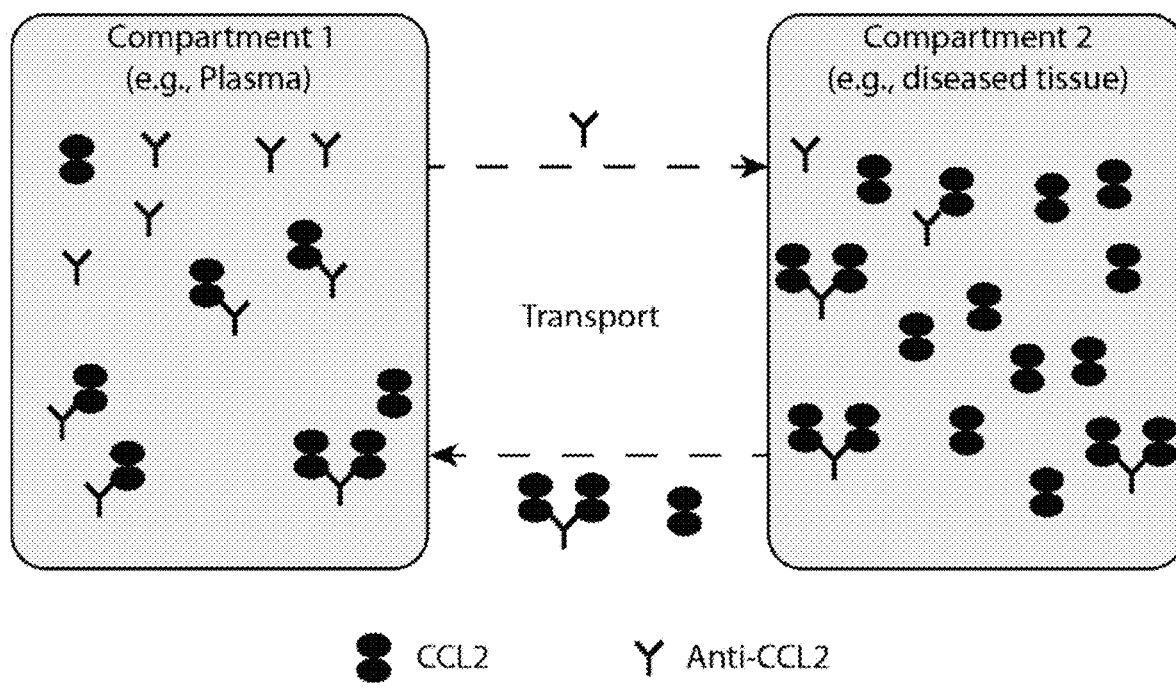
FIG. 4 illustrates an exemplary diagram depicting CCL2 targeting in plasma and in diseased tissue.

Monoclonal antibodies injected intravenously typically binds CCL2 in plasma and forms a complex before they reach diseased tissues, resulting in wasted monoclonal antibodies. Bi-specific mAbs allow us to sequester mAb in diseased tissue with a "free" anti-CCL2 arm to bind to tissue CCL2, which provides tissue specific targeting of CCL2 (See FIG. 4). We can design the affinity for CCL2 such that it does not bind to serum CCL2 but binds tissue CCL2. Furthermore, we can also compete with the 60 pM affinity for CCR2 by increasing dose. Thus, this approach allows us preferentially inhibit tissue CCL2 as opposed to plasma CCL2, resulting in highly effective treatment of scleroderma.

Figure 5:
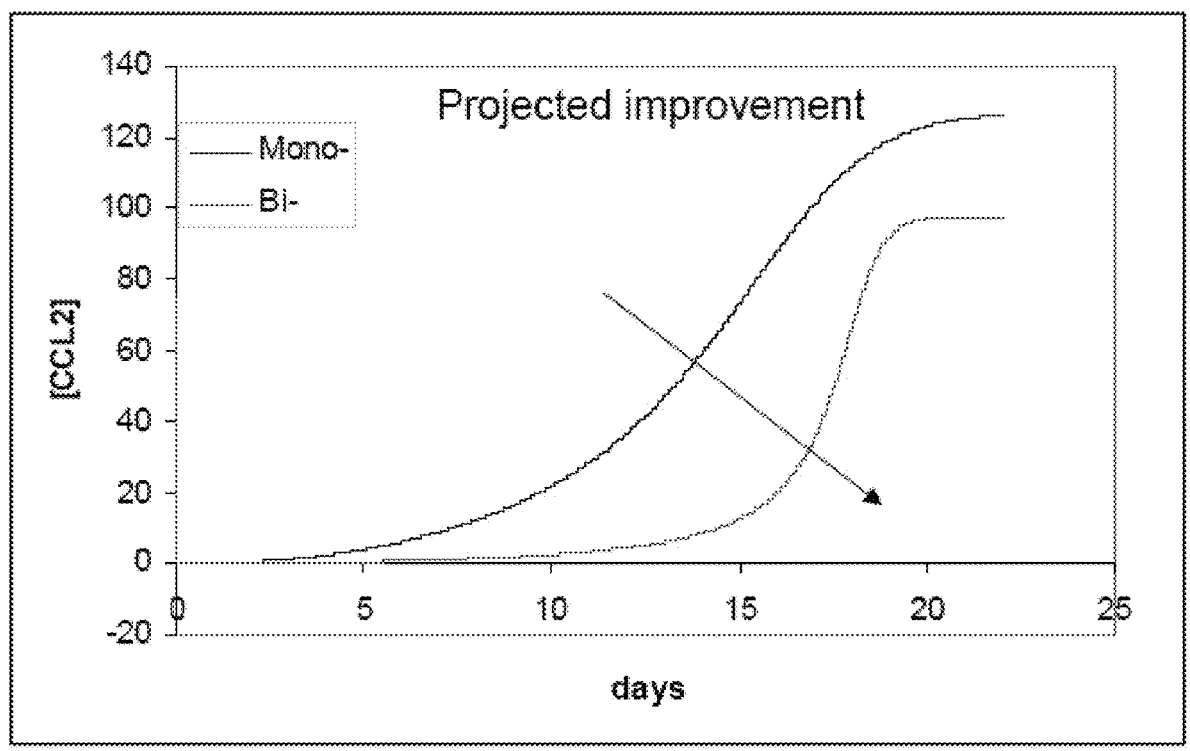
FIG. 5 depicts an exemplary graph plotting concentration of CCL2 as a function of days post treatment with either anti-CCL2 (Mono) or anti-CCL2/LOXL2 (Bi), illustrating preliminary bi-specific modeling results.

A preliminary set of results from modeling bi-specific binding proteins are shown in FIG. 5 based on the following assumptions: Anti-LOXL2 arm has a kd of 1 pM or better; anti-CCL2 arm has a kd ranging between 500 pM and 1 nM; and LOXL2 bound mAb is not internalized or degraded.

Example 5: Clinical Design

Based upon the success of animal treatments, Phase I-III dose ranging and single dose studies of anti-CCL2/LOXL2 bi-specific antibody detailed in Tables 3-7 are designed in healthy individuals and individuals with different stages of scleroderma to evaluate the safety, tolerability, efficacy, and pharmacokinetics of anti-CCL2/LOXL2.

A primary objective of Human Clinical Trial 1 includes determining the safety of 4 dose levels of anti-CCL2/LOXL2 antibody administered in healthy individuals. Secondary objectives include evaluating the pharmacokinetics of 4 different dose levels of anti-CCL2/LOXL2 antibody administered in healthy individuals. A detailed protocol synopsis of this clinical trial is shown in Table 3.

TABLE 3

| Human Clinical Trial 1 | |
|---|---|
| Phase | Phase 1 |
| # of Trials | 1 |
| Patient Population | Healthy volunteers |
| Trial Design and Endpoints | Single dose, dose escalation |
| | Primary: Safety |
| | Secondary: PK |
| # of Subjects | 4 dose groups |
| | n = 4 each |
| | 16 subjects total |
| Trial Length (FPI to LPV) | 0.5 years |
| | ~6 weeks to dose |
| | ~15 weeks follow up for PK |
| Comments | Single Phase 1 unit |

A primary objective of Human Clinical Trial 2 includes determining the safety of 4 dose levels of anti-CCL2/LOXL2 antibody administered in individuals with early symptoms of scleroderma. Secondary objectives include (1) to determine the pharmacokinetics of 4 different dose levels of anti-CCL2/LOXL2 antibody administered in individuals with early symptoms of scleroderma (2) to determine the pharmacodynamic (PD) response of individuals with early symptoms of scleroderma to 4 different dose levels of anti-CCL2/LOXL2 antibody by assaying gene expression in sequential skin biopsies and (3) to determine the clinical response of individuals with early symptoms of scleroderma to 4 different dose levels of anti-CCL2/LOXL2 antibody as measured by the Modified Rodnan Skin Score (mRSS). A detailed protocol synopsis of this clinical trial is shown in Table 4.

TABLE 4

Human Clinical Trial 2

| | |
|---|---|
| Phase | Phase 1/2 |
| # of Trials | 1 |
| Patient Population | Early (<2 yrs since non- Raynaud's Phenomenon (RP) symptom onset) diffuse SSc mRSS ≥ 15 |
| Trial Design and Endpoints | Multiple Dose Escalation<br>Double-blind placebo-controlled<br>Treatment duration: 6 months<br>4 Dose levels<br>Primary: Safety<br>Secondary: PK<br>PD response (sequential skin biopsy gene expression - baseline, 4 wks, 6 months)<br>Clinical response (mRSS) |
| # of Subjects | 4 dose groups<br>n = 10 each (8 active/2 placebo)<br>40 subjects total |
| Trial Length (FPI to LPV) | 1.5 years |
| Comments | Up to 8 sites to recruit within 1 yr |

A primary objective of Human Clinical Trial 3 includes determining the efficacy of a single dose level of anti-CCL2/LOXL2 antibody administered in individuals with early symptoms of scleroderma as measured by the Modified Rodnan Skin Score (mRSS). Secondary objectives include (1) determining the efficacy of a single dose level of anti-CCL2/LOXL2 antibody administered in individuals with early symptoms of scleroderma as measured by the Health Assessment Questionnaire-Disability Index (HAQ-DI) and (2) determining the efficacy of a single dose level of anti-CCL2/LOXL2 antibody administered in individuals with early symptoms of scleroderma as measured by organ specific assessments. A detailed protocol synopsis of this clinical trial is shown in Table 5.

TABLE 5

Human Clinical Trial 3

| | |
|---|---|
| Phase | Phase 2 |
| # of Trials | 1 |
| Patient Population | Early (<2 yrs since non- Raynaud's Phenomenon (RP) symptom onset) diffuse SSc mRSS ≥ 15 |
| Trial Design and Endpoints | 1 dose level<br>Double-blind Placebo Controlled Parallel Group<br>Treatment duration 6 months<br>Open-label extension<br>Primary: mRSS<br>Secondary: HAQ DI, organ-specific assessments |
| # of Subjects | 2:1 randomization<br>120 subjects total |
| Trial Length (FPI to LPV) | 1.5 years |
| Comments | Up to 20 sites to recruit within 1 yr |

A primary objective of Human Clinical Trial 4 includes determining the efficacy relative to oral cyclophosphamide of a single dose level of anti-CCL2/LOXL2 antibody administered in individuals with limited or diffuse scleroderma with lung disease as measured by Forced Vital Capacity (FVC). Secondary objectives include (1) determining the efficacy relative to oral cyclophosphamide of a single dose level of anti-CCL2/LOXL2 antibody administered in individuals with limited or diffuse scleroderma with lung disease as measured by the HAQ-DI, (2) determining the efficacy relative to oral cyclophosphamide of a single dose level of anti-CCL2/LOXL2 antibody administered in individuals with limited or diffuse scleroderma with lung disease as measured by the mRSS, and (3) determining the efficacy relative to oral cyclophosphamide of a single dose level of anti-CCL2/LOXL2 antibody administered in individuals with limited or diffuse scleroderma with lung disease as measured by diffusing capacity of the lung for carbon monoxide (DLCO). A detailed protocol synopsis of this clinical trial is shown in Table 6.

TABLE 6

Human Clinical Trial 4

| | |
|---|---|
| Phase | Phase 2 |
| # of Trials | 1 |
| Patient Population | Limited or Diffuse SSc with lung disease:<br>Active alveolitis by HRCT<br><7 yrs since non-RP symptom onset<br>FVC < 85% > 45% predicted |
| Trial Design and Endpoints | 1 dose level<br>Double-blind Controlled Parallel Group<br>Comparator: SoC (oral cyclophosphamide)<br>Treatment duration 12 months<br>Open-label extension<br>Primary: FVC<br>Secondary: DLCO, HAQ DI, mRSS |
| # of Subjects | 2:1 randomization<br>120 subjects total |
| Trial Length (FPI to LPV) | 1.5 years |
| Comments | Up to 10 sites to recruit within 6 months |

Objective of Human Clinical Trial 5 include (1) determining the efficacy relative to oral cyclophosphamide of a single dose level of anti-CCL2/LOXL2 antibody administered in individuals with early symptoms of scleroderma and/or limited or diffuse scleroderma with lung disease as measured by Forced Vital Capacity (FVC), (2) determining the efficacy relative to oral cyclophosphamide of a single dose level of anti-CCL2/LOXL2 antibody administered in individuals with early symptoms of scleroderma and/or limited or diffuse scleroderma with lung disease as measured by the HAQ-DI, (3) determining the efficacy relative to oral cyclophosphamide of a single dose level of anti-CCL2/LOXL2 antibody administered in individuals with early symptoms of scleroderma and/or limited or diffuse scleroderma with lung disease as measured by mRSS, and (4) determining the efficacy relative to oral cyclophosphamide of a single dose level of anti-CCL2/LOXL2 antibody administered in individuals with early symptoms of scleroderma and/or limited or diffuse scleroderma with lung disease as measured by DLCO. A detailed protocol synopsis of this clinical trial is shown in Table 7.

TABLE 7

Human Clinical Trial 5

| | |
|---|---|
| Phase | Phase 3 |
| # of Trials | 1 each |
| Trial Design and Endpoints | Single dose level, double-blind head-to- head comparison with SoC in either or both early dSSc or SSc Lung Disease, depending on outcome of Phase 2s<br>Endpoints as in Phase 2 |

TABLE 7-continued

Human Clinical Trial 5

| | |
|---|---|
| Phase | Phase 3 |
| # of Subjects | 120 patients each |
| Trial Length (FPI to LPV) | 2.0 years |
| | 0.5 to 1 year enrollment period |
| Comments | Treatment duration 12 months |

Patients exhibiting early symptoms of scleroderma treated with anti-CCL2/LOXL2 antibody are expected to demonstrate significant improvement of symptoms as measured by the mRSS and HAQ-DI. Patients with limited or diffuse scleroderma with lung disease treated with anti-CCL2/LOXL2 antibody are expected to demonstrate significant improvement of symptoms as measured by the mRSS, HAQ-DI, and FVC. Anti-CCL2/LOXL2 antibody is expected to be more effective than cyclophosphamide in treatment of patients either with early symptoms of scleroderma or with limited or diffuse scleroderma with lung disease as measured by mRSS, HAQ-DI, and/or FVC.

Example 6: In Vivo Efficacy of Anti-CCL2 and Anti-LOXL2 Combination Therapy in Bleomycin-Induced Fibrosis This example describes the effect of treatment of inflammation and fibrosis with a combination of monospecific anti-CCL2 and anti-LOXL2 antibodies in an animal model of scleroderma over a two-week time course. The evaluation of monotherapy using either an anti-CCL2 or an anti-LOXL2 antibody and combination therapy (both anti-CCL2 and anti-LOXL2 antibodies) in a murine model of fibrosis was performed. A chronic bleomycin 14-day mini-osmotic subcutaneous pump was used with skin and lung fibrosis as outcomes for drug efficacy. As shown below, combination therapy with both antibodies demonstrated a significant effect in both skin and lung fibrosis.

Briefly, a bleomycin 14-day pump murine SSc-skin and lung fibrosis model was used to test the efficacy of the drugs. Groups (n=5; 8-10 weeks) of female C57BL/6 mice were exposed subcutaneously to bleomycin (90 U/Kg) or PBS (n=3 mice) via osmotic pump for 7 days with skin and lungs harvested on day 14. Bleomycin exposed mice were treated intraperitoneally with anti-CCL2 (dose 2 mg/Kg/2×/week), anti-LOXL2 (dose 15 mg/Kg/2×/week) or IgG-control (dose 17 mg/Kg/2×/week) twice a week starting on the day of the pump insertion until day 14. Treatment groups are set forth in Table 8.

TABLE 8

| Treatment Group | Description |
|---|---|
| PBS | mini-osmotic pumps with PBS only |
| IgG | mini-osmotic pumps with bleomycin, IgG/IP/2x/week |
| anti-CCL2 | mini-osmotic pumps with bleomycin, anti-CCL2/IP/2x/week |
| anti-LOXL2 | mini-osmotic pumps with bleomycin, anti-LOXL2/IP/2x/week |
| Both | mini-osmotic pumps with bleomycin, anti-CCL2 and anti-LOXL2/IP/2x/week |

Outcomes Measures for Cutaneous Fibrosis

To determine drug efficacy in dermal fibrosis, skin was analyzed by hematoxylin-eosin (H&E) and collagen deposition by Masson's trichrome staining. In addition, the presence of ulcers was assessed clinically and the skin thickness was measured by the maximal distance between the epidermal-dermal junction and the dermal-subcutaneous fat junction in four different skin sections from each mouse using Olympus DP70 camera and OLYMPUS® Micro Suite Basic software. Tissue sections were analyzed by a blinded investigator.

Outcome Measures for Lung Fibrosis

To determine drug efficacy in lung fibrosis, histology and gene expression were analyzed. Insufflated lungs were fixed in formalin, embedded in paraffin, and stained with H&E, Masson's trichrome staining, and Arginase-1. The Aschroft score (Ashcroft et al., 1988, *J. Clin. Pathol.* 41:467-470) was blindly analyzed in all groups after Masson's staining. Arginase-1 staining was also blindly scored from zero to four in at least four sections per slides. The average of Aschroft and Arginase-1 scores in each mouse was used as the final score.

Statistical Analysis

Comparison of gene expressions, histological analysis of specific staining and lung score was analyzed by One-Way ANOVA and Bonferroni's multiple comparison post-tests. Two-group comparisons was analyzed by Student T-test. Microarray analysis followed standard false discovery rate (FDR) of less than 10%, comparing treated samples with controls. P-values less than or equal to 0.05 were considered statistically significant.

Results

Cutaneous Fibrosis

Figure 6:
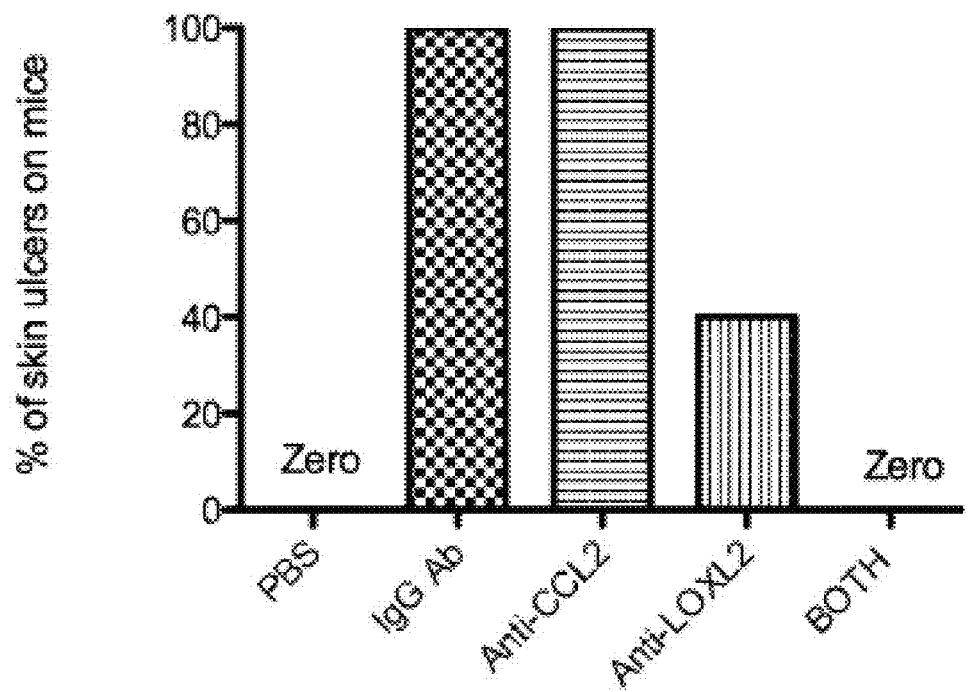
FIG. 6 shows the percentage of skin ulcers observed in C57BL/6 mice treated with IgG, anti-CCL2 antibody, anti-LOXL2 antibody, or anti-CCL2 and anti-LOXL2 antibodies. PBS: negative control. BOTH: combination treatment with anti-CCL2 antibody and anti-LOXL2 antibody.
Figure 7:
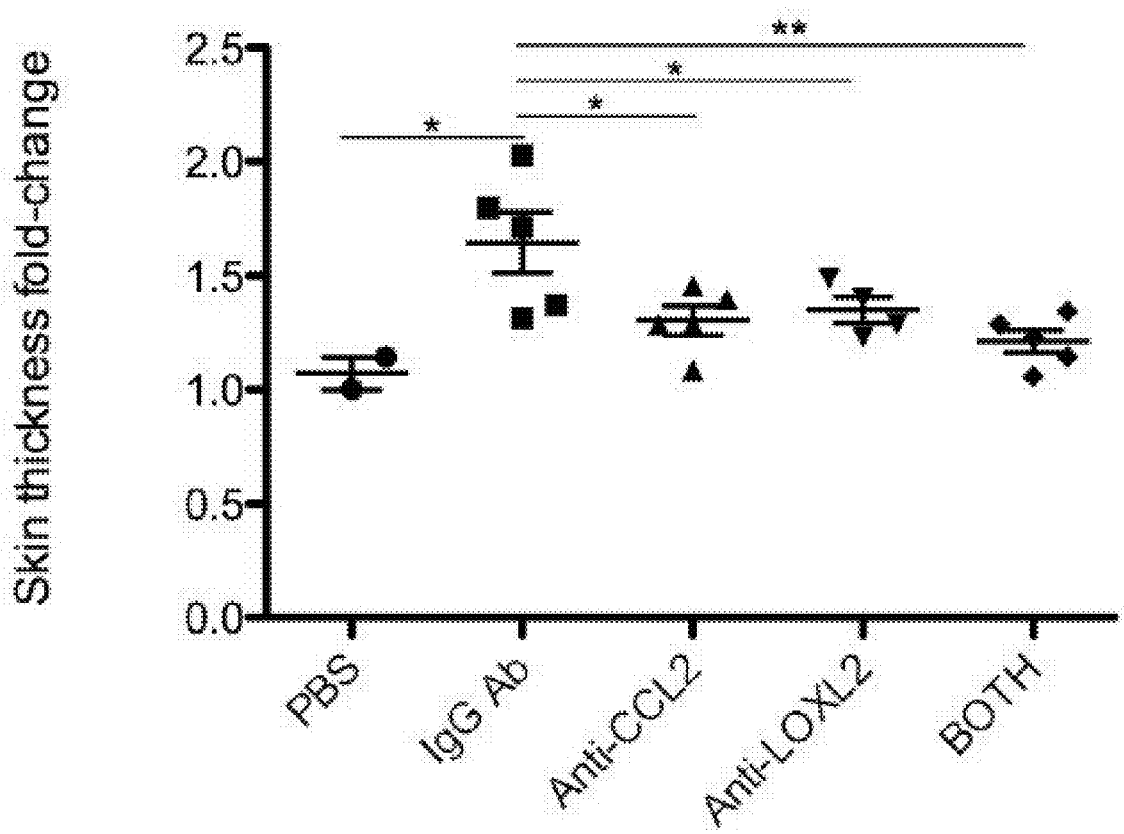
FIG. 7 shows the fold-change in skin thickness observed in C57BL/6 mice treated with IgG, anti-CCL2 antibody, anti-LOXL2 antibody, or anti-CCL2 and anti-LOXL2 antibodies. PBS: negative control. BOTH: combination treatment with anti-CCL2 antibody and anti-LOXL2 antibody.

The surgical procedure to implant the mini-osmotic pumps was overall well tolerated in mice. One mouse in the PBS treatment group died after 18 hours, which was likely attributed to anesthesia. FIG. 6 shows the percentage of skin ulcers observed in each treatment group. FIG. 7 shows the thickness of skin tissue samples measured for each treatment group.

As shown in FIG. 6, none of the mice treated with PBS developed skin ulcers. In contrast, all the mice exposed to bleomycin and treated with IgG (control) or anti-CCL2 developed skin ulcers, while only two mice exposed to bleomycin and treated with anti-LOXL2 developed skin ulcers. In the combination treatment group, none of the mice developed skin ulcers.

As shown in FIG. 7, skin thickness was strongly suppressed in both mono- and combination therapy (anti-CCL2, anti-LOX2, Both) groups as compared to control (IgG). The average fold-change for each group is set forth in Table 9.

TABLE 9

| Treatment group | Average fold-change skin thickness |
|---|---|
| PBS | 1.07 |
| IgG | 1.64 |
| anti-CCL2 | 1.30 |
| anti-LOXL2 | 1.34 |
| Both | 1.21 ($p < 0.001$) |

Lung Fibrosis

Figure 8:
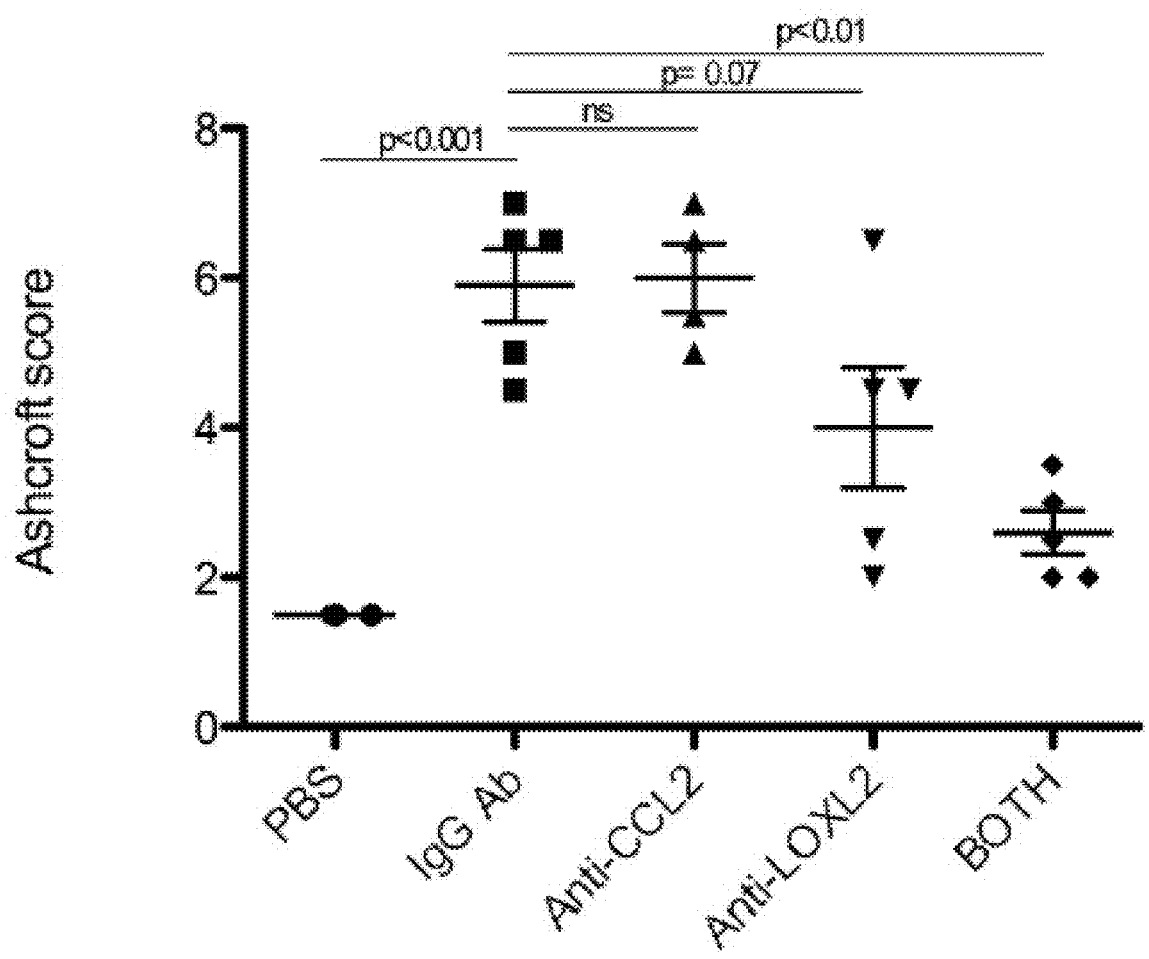
FIG. 8 shows the Ashcroft score for lung tissue samples of C57BL/6 mice treated with IgG, anti-CCL2 antibody, anti-LOXL2 antibody, or anti-CCL2 and anti-LOXL2 antibodies. PBS: negative control. BOTH: combination treatment with anti-CCL2 antibody and anti-LOXL2 antibody.

Lung tissue samples were scored using the Ashcroft method (as described above; FIG. 8). The Aschroft score was blindly analyzed in the lungs of all five treatment groups (Table 8). The average of the Aschroft score for each treatment group is set forth in Table 10. Using the ANOVA analysis for all treatment groups, only the combination treatment group (Both) was statistically reduced as compared to control (IgG; $p<0.01$). A Student T-test comparing control (IgG) and anti-CCL2 groups was not significant, whereas control as compared to anti-LOXL2 treatment group showed a trend (p=0.07). Control versus combination treatment group was reduced (p<0.01).

TABLE 10

| Treatment group | Average Aschroft Score |
| --- | --- |
| PBS | 1.5 |
| IgG | 5.76 |
| anti-CCL2 | 4.87 |
| anti-LOXL2 | 3.38 |
| Both | 2.64 (p < 0.01) |

Arginase-1 Lung Staining

Figure 9:
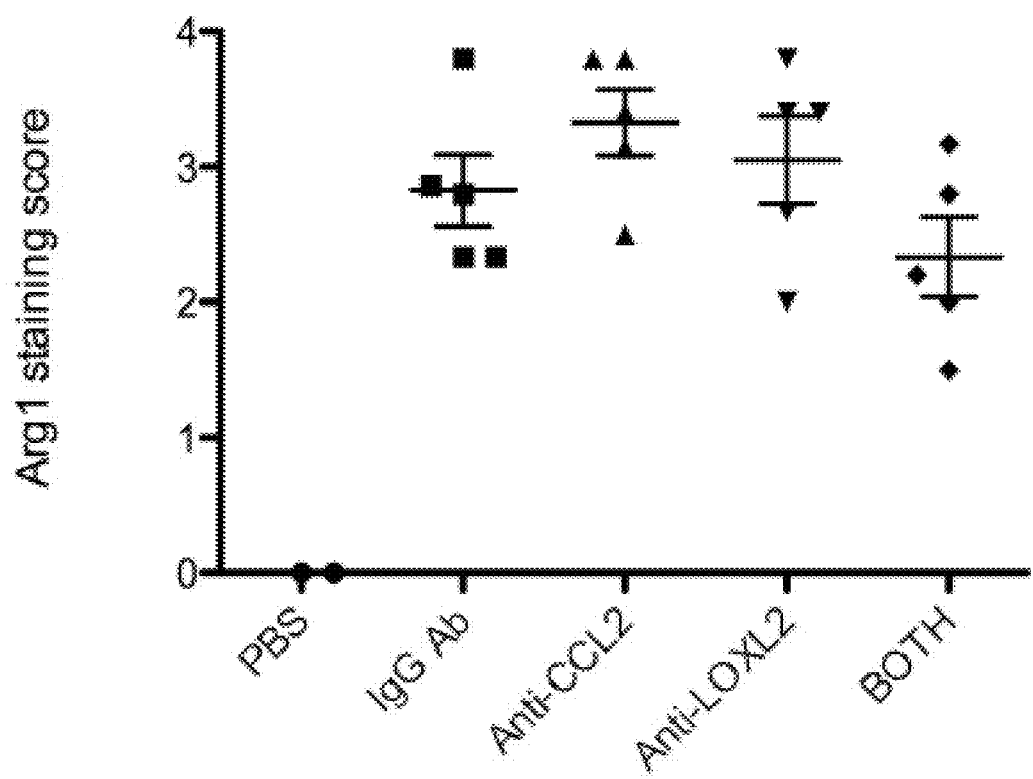
FIG. 9 shows Arginase 1 (Arg1)-staining in lung tissue samples of C57BL/6 mice treated with IgG, anti-CCL2 antibody, anti-LOXL2 antibody, or anti-CCL2 and anti-LOXL2 antibodies. PBS: negative control. BOTH: combination treatment with anti-CCL2 antibody and anti-LOXL2 antibody.

Staining for Arginase 1 (Arg1), a specific marker for macrophage activation, was also performed on lung tissue samples for each treatment group (FIG. 9). The inventors have previously observed that the bleomycin chronic model demonstrates a strong activation of macrophages in the lungs based on CD163 staining, which is almost abolished in CCL2-deficient mice. Therefore, since the peak of cell influx into the lungs is known to happen on day-14 of the bleomycin model, analysis of $CD163^+$ expression in lung cells from all bleomycin-exposed groups after treatments was performed. Strong expression of $CD163^+$ was confirmed in the lungs after exposure to bleomycin.

Figure 10:
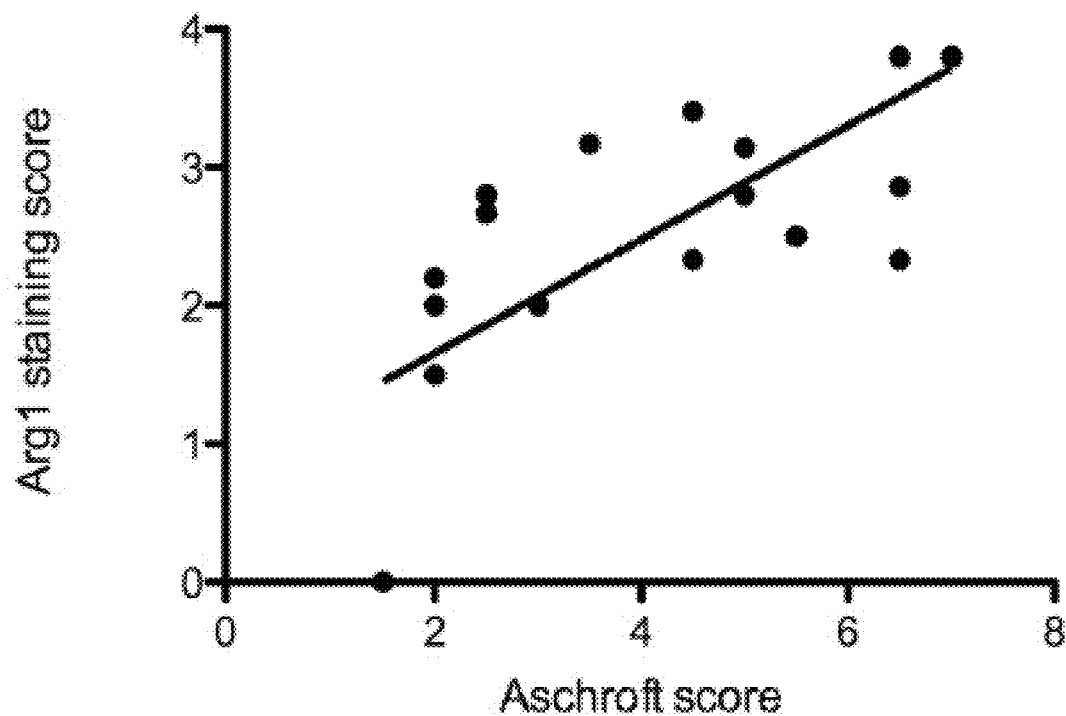
FIG. 10 shows a correlation plot of Arginase 1 (Arg1)-staining as a function of Ashcroft score in lung tissue samples of C57BL/6 mice treated with IgG, anti-CCL2 antibody, anti-LOXL2 antibody, or anti-CCL2 and anti-LOXL2 antibodies. PBS: negative control. BOTH: combination treatment with anti-CCL2 antibody and anti-LOXL2 antibody.
Figure 11:
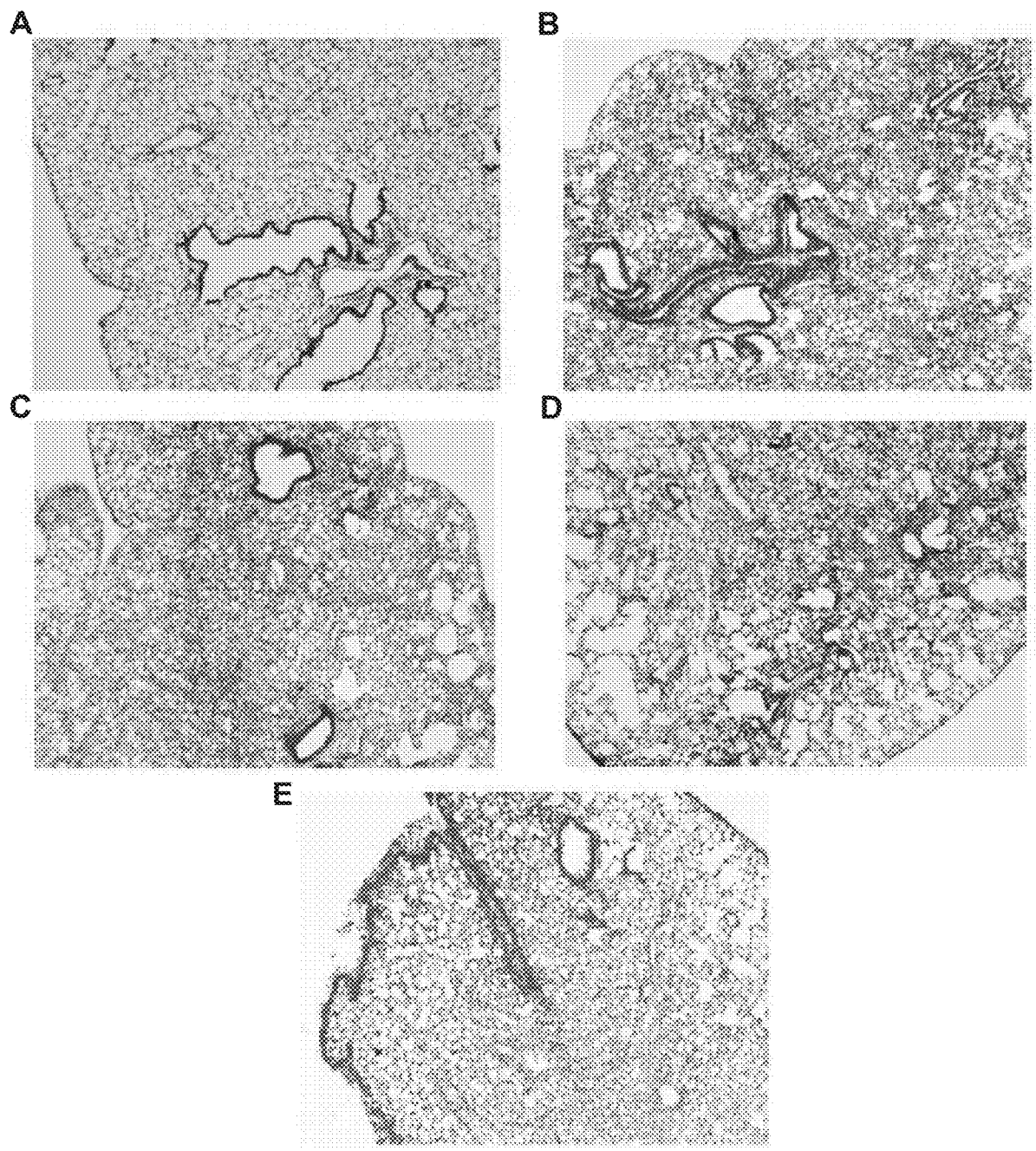
FIG. 11 shows representative histological sections of lung tissue samples stained with Trichrome for various treatment groups of mice at 4× power. Top row: PBS (A), IgG (B). Middle row: anti-CCL2 (C), anti-LOXL2 (D). Bottom row: anti-CCL2 and anti-LOXL2 (E).
Figure 12:
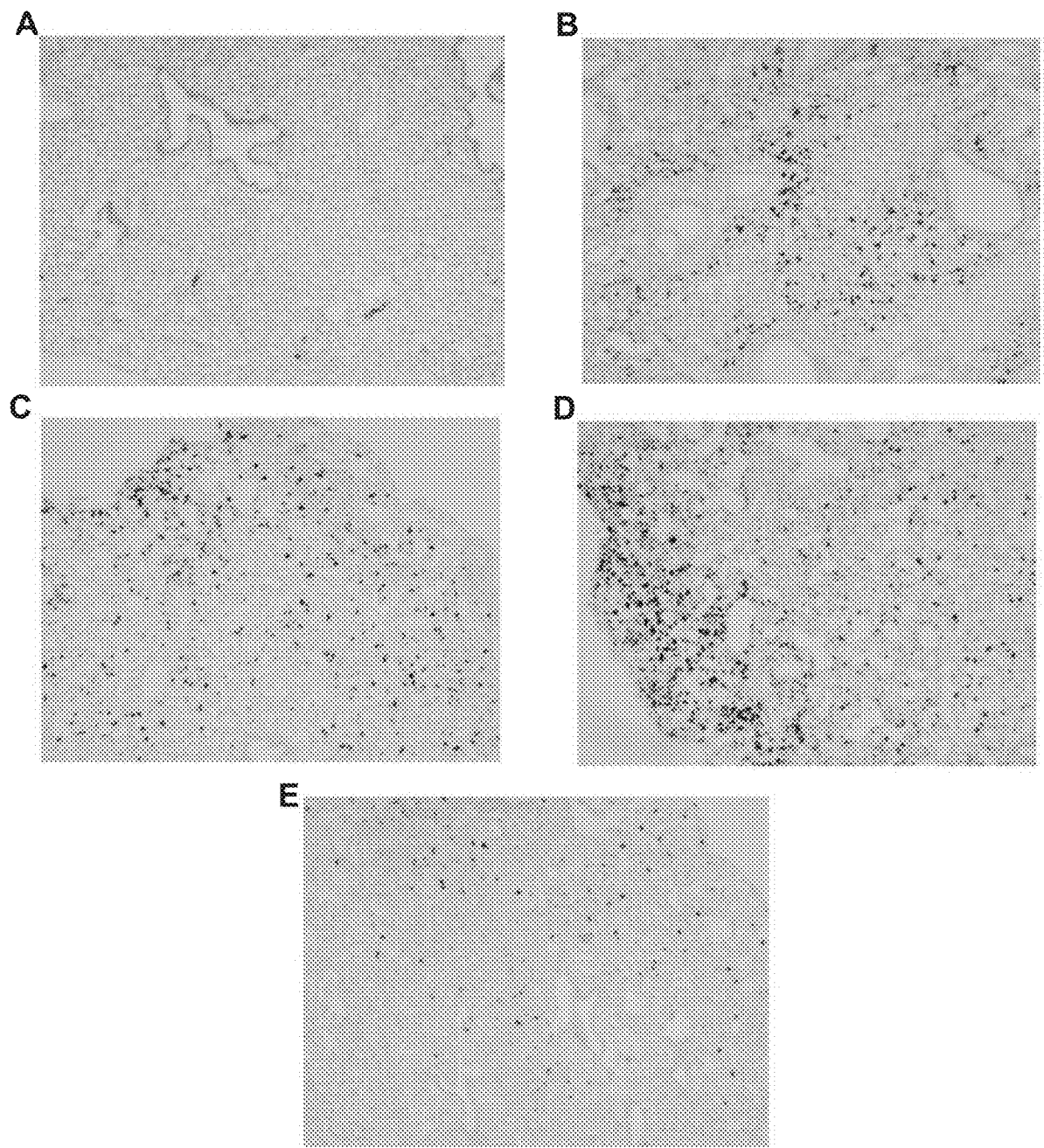
FIG. 12 shows representative histological sections of lung tissue samples stained with Arginase 1 (Arg1) for various treatment groups of mice. Top row: PBS (A), IgG (B). Middle row: anti-CCL2 (C), anti-LOXL2 (D). Bottom row: anti-CCL2 and anti-LOXL2 (E).
Figure 13:
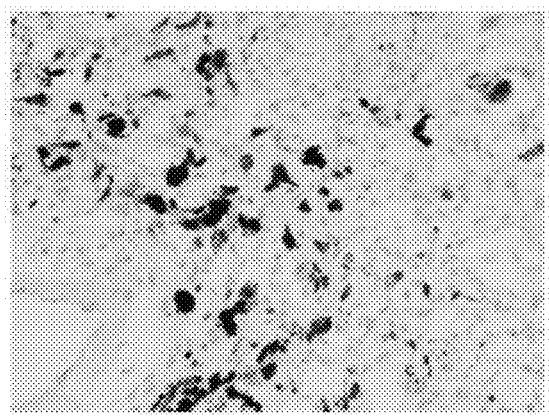
FIG. 13 shows representative histological sections of lung tissue samples stained with Arginase 1 (Arg1) for IgG treatment groups at 20× (A) and 40× (B) power.
Figure 13:
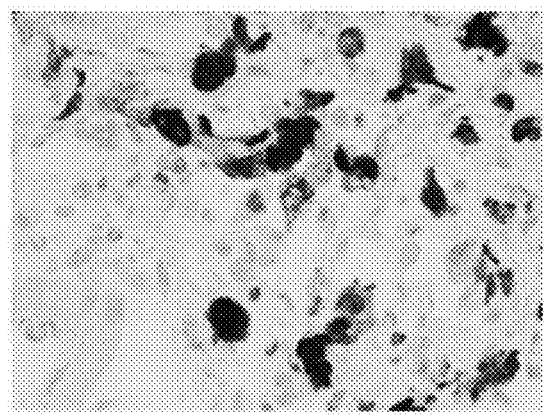

Arginase-1 expression was blindly quantified in at least four sections in the lungs of each mouse. The average Arginase-1 score for each treatment group is set forth in Table 11. Arginase-1 staining was strongly correlated with Aschroft score (FIG. 10). FIG. 11 shows histological sections of lung tissue samples stained with Trichrome. FIGS. 12 and 13 shows histological sections of lung tissue samples stained with Arginase 1 (Arg1).

TABLE 10

| Treatment group | Average Arg1 Score |
| --- | --- |
| PBS | 0 |
| IgG | 2.82 |
| anti-CCL2 | 3.32 |
| anti-LOXL2 | 3.05 |
| Both | 2.01 (p = 0.06) |

As shown in this example, all mice in the IgG and anti-CCL2 treatment groups contained skin ulcers. However, only 2 of 5 mice in the anti-LOXL2 treatment group contained skin ulcers. Interestingly, the treatment group that received both anti-CCL2 and anti-LOXL2 antibodies did not show any ulcers in the harvested skin tissue (see FIG. 6). Analysis of variance (ANOVA) confirmed that the reduction in skin thickness for both mono-treatment (either anti-CCL2 or anti-LOXL2 alone) and combination treatment (anti-CCL2 and anti-LOXL2 together) was significant as compared to the IgG treatment group (see FIG. 7). Therefore, treatment of fibrotic disease by combination therapy with anti-CCL2 and anti-LOXL2 antibodies was effective to stop the formation of skin ulcers, and effective to reduce the thickening of skin tissue, in mice treated with bleomycin.

Further, ANOVA also confirmed that combination therapy with anti-CCL2 and anti-LOXL2 antibodies significantly reduced the degree of fibrosis in lung tissue samples (Aschroft score of about 2) as compared to the IgG treatment group (Aschroft score of about 6) (see FIG. 8). Combination therapy with anti-CCL2 and anti-LOXL2 antibodies demonstrated the lowest level of macrophage activation in lungs of all four treatment groups (Arg1-staining, see FIG. 9).

Taken together, these data demonstrate that treatment with anti-CCL2, anti-LOXL2 alone or in combination in the bleomycin 14-day murine model showed reduction of cutaneous and/or lung fibrosis with the strongest effect in the skin and in the lungs observed when treating with an anti-LOXL2 antibody or a combination of anti-CCL2 and anti-LOXL2 antibodies. Thus, anti-CCL2 and anti-LOXL2 antibodies can be administered in combination to effectively treat and/or ameliorate one or more symptoms of a fibrotic or related inflammatory disease (e.g., scleroderma), disorder or condition.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any HCV genotype/subtype, any HCV antibody, any epitope, any pharmaceutical composition, any method of administration, any therapeutic application, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

We claim:

1. A method of treating human skin ulcers due to scleroderma comprising administering to a human subject having skin ulcers due to scleroderma a therapeutically effective amount of
    an anti-CCL2 antibody, or fragment thereof, that binds to human CCL2 protein; and
    an anti-LOXL2 antibody, or fragment thereof, that binds to human LOXL2 protein,
    wherein the administration leads to reduced skin ulcers in the human subject relative to an untreated human subject individual who has skin ulcers due to scleroderma.

2. The method of claim 1, wherein the anti-CCL2 antibody, or fragment thereof, has a binding affinity of 1 pM or greater.

3. The method of claim 1, wherein the anti-LOXL2 antibody, or fragment thereof is selected from the group consisting of intact IgG, F(ab')2, F(ab)2, Fab', Fab, ScFvs, diabodies, triabodies and tetrabodies.

4. The method of claim 1, wherein one or both of the anti-CCL2 antibody, or fragment thereof, and the anti-LOXL2 antibody, or fragment thereof, are humanized.

* * * * *